(12) United States Patent
Lin

(10) Patent No.: US 11,965,259 B2
(45) Date of Patent: Apr. 23, 2024

(54) INTEGRATED HYDROGEN GAS GENERATOR WITH HYDROGEN WATER MODULE

(71) Applicant: SHANGHAI ASCLEPIUS MEDITEC CO., LTD., Shanghai (CN)

(72) Inventor: Hsin-Yung Lin, Shanghai (CN)

(73) Assignee: Shanghai Asclepius Meditec Co., Ltd., Shanghai (CN)

( * ) Notice: Subject to any disclaimer, the term of this patent is extended or adjusted under 35 U.S.C. 154(b) by 630 days.

(21) Appl. No.: 16/867,037

(22) Filed: May 5, 2020

(65) Prior Publication Data

US 2020/0352985 A1    Nov. 12, 2020

(30) Foreign Application Priority Data

May 7, 2019    (TW) .................................. 108115736

(51) Int. Cl.
*C25B 15/08*    (2006.01)
*A61M 16/00*    (2006.01)
(Continued)

(52) U.S. Cl.
CPC ......... *C25B 15/085* (2021.01); *A61M 16/021* (2017.08); *A61M 16/10* (2013.01);
(Continued)

(58) Field of Classification Search
CPC ...................................................... C25B 1/04
See application file for complete search history.

(56) References Cited

U.S. PATENT DOCUMENTS

2013/0206586 A1    8/2013    Lin
2016/0108528 A1*    4/2016    Lin ....................... C02F 1/4618
                                                                    204/278
(Continued)

FOREIGN PATENT DOCUMENTS

CN    203291353 U    11/2013
CN    205527886 U    8/2016
(Continued)

OTHER PUBLICATIONS

Notice of Search Report and Written Opinion for Foreign Corresponding Patent Application No. 10-2020-0054072 dated Feb. 24, 2022.
(Continued)

*Primary Examiner* — Harry D Wilkins, III
(74) *Attorney, Agent, or Firm* — Rosenberg, Klein & Lee

(57) ABSTRACT

An integrated hydrogen gas generator with hydrogen water module comprises a water tank, an electrolytic module, an integrated flow channel device, a humidifying module, and a hydrogen water module. The electrolytic module is configured to electrolyze the water in the water tank to generate a gas comprising hydrogen. The water tank, the humidifying module, and the hydrogen water module are respectively coupled to the integrated passageway module so that the water and the gas comprising hydrogen flow in a special sequence between them. The humidifying module is configured to humidify the gas comprising hydrogen. The hydrogen water module is configured for accommodating liquid and receiving the gas comprising hydrogen into the liquid to form a liquid comprising hydrogen. The configuration of pipeline is replaced by the integrated passageway module in the integrated hydrogen gas generator of the present invention.

19 Claims, 22 Drawing Sheets

(51) Int. Cl.
- *A61M 16/10* (2006.01)
- *A61M 16/16* (2006.01)
- *C01B 3/50* (2006.01)
- *C25B 1/04* (2021.01)
- *C25B 9/00* (2021.01)

(52) U.S. Cl.
CPC ...... *A61M 16/1005* (2014.02); *A61M 16/105* (2013.01); *A61M 16/16* (2013.01); *C01B 3/506* (2013.01); *C25B 1/04* (2013.01); *C25B 9/00* (2013.01); *C25B 15/08* (2013.01); *Y02E 60/36* (2013.01)

(56) References Cited

U.S. PATENT DOCUMENTS

| | | | |
|---|---|---|---|
| 2016/0263535 A1* | 9/2016 | Lin | B01F 23/23123 |
| 2018/0002824 A1 | 1/2018 | Lin | |
| 2018/0228995 A1 | 8/2018 | Lin | |
| 2019/0062933 A1 | 2/2019 | Lin | |

FOREIGN PATENT DOCUMENTS

| | | |
|---|---|---|
| CN | 107551374 A | 1/2018 |
| CN | 105624723 B | 11/2018 |
| CN | 108950588 A | 12/2018 |
| CN | 109364345 A | 2/2019 |
| CN | 105617503 B | 4/2019 |
| EP | 3095764 A1 | 11/2016 |
| JP | H09-504053 A | 4/1997 |
| JP | 2016108657 A | 6/2016 |
| JP | 2018031070 A | 3/2018 |
| JP | 2018525525 A | 9/2018 |
| JP | 2018165396 A | 10/2018 |
| KR | 20180051517 A | 5/2018 |
| RU | 2614359 C2 | 3/2017 |
| RU | 2644348 C2 | 2/2018 |
| TW | M518089 U | 3/2016 |

OTHER PUBLICATIONS

Examination report for counterpart European Application 20172885.4, dated Jan. 10, 2020.
Examination report for counterpart Indian Application 202024018503, dated Jan. 12, 2020.
Notice of Search Report and Written Opinion for Foreign Corresponding Patent Application No. 2020081480 dated Oct. 4, 2021.
Office Action and Search Report for counterpart Russian Application No. 2020115411, dated Mar. 10, 2021.
Notice of Search Report and Written Opinion for Corresponding SG Patent Application No. 10202004106U dated Dec. 8, 2020.

* cited by examiner

INTEGRATED HYDROGEN GAS GENERATOR WITH HYDROGEN WATER MODULE

BACKGROUND OF THE INVENTION

Field of the Invention

The invention is related to a generator for generating gas comprising hydrogen and hydrogen liquid, and more particularly, related to an integrated hydrogen gas generator having a hydrogen water module and an integrated passageway module for integrating connection of the units therein.

Description of the Prior Art

From then till now, humans have dedicated a plenty of research for prolonging human lifetime, and many health developments in medical technology have targeted on treating diseases. Nowadays, medical technology developments focus on preventive medicines more than passive disease treatments which treat the disease when it occurs, wherein the preventive medicines may include health foods research, screening for hereditary disease and prevent treatment for avoiding risk factor. Besides extending lifespan of humans, various anti-agents and anti-oxidation technologies comprising smearing skin care and anti-oxidation foods and medicines are gradually developed and widely applied.

Studies have found that the human body produces unstable oxygen (O+), also known as free radicals (harmful free radicals), for various reasons, such as disease, diet, environment or one's lifestyle. The free radicals are a single atom, molecule, or ion that has an unpaired valence electron. The free radicals attack human's cell membrane, cell and tissue to obtain electrons from other atom, resulting in chain peroxidation reaction in vivo. Peroxidation reaction generates degenerative syndromes in human body, such as blood vessel became fragility, brain cell aging, immune system degeneration, cataracta, degenerative arthritis, anetoderma and generalized aging. Many researches display small molecular of rich-hydrogen water, so it can easily enter the cell and be absorbed, to participate human metabolism, and accelerate cell detoxification. Drinking rich-hydrogen water can indirectly reduce amount of free radicals in human body to change acidic body of human to alkaline body, and also achieve the elimination of chronic disease and affection of beauty health.

In the recent technology, the gas comprising hydrogen and the hydrogen liquid are respectively generated by the hydrogen gas generator and the hydrogen liquid generator, and then the users need to purchase at least two kinds of devices to obtain the gas comprising hydrogen and the hydrogen liquid. Moreover, the existing generator for hydrogen liquid only can produce water comprising hydrogen instead of other kinds of liquids comprising hydrogen. The existing generator for hydrogen liquid electrolyzes the electrolyte water to generate hydrogen ions, and collects the hydrogen ions to form the hydrogen gas and input the hydrogen gas into the electrolyte water to generate the said water comprising hydrogen. This will make it difficult for the users who do not like to drink water continuously drink the water comprising hydrogen, and even discourage users from using it.

In addition, in the recent technology, each unit in the generator need to be connected by pipelines, which causes the cumbersome assembly process of the generator, complicated wiring, large volume of the generator, and dropping, gas leakage, and water leakage problems of the pipeline.

SUMMARY OF THE INVENTION

In view of this, the present invention provides an integrated hydrogen gas generator with a hydrogen water module to solve the problems of the prior art. According to an embodiment of the present invention, an integrated hydrogen gas generator with hydrogen water module of the present invention comprises a water tank, an electrolytic module, an integrated passageway module, a humidification module, and a hydrogen water module. The water tank is configured to accommodate electronic water. The electrolytic module is configured to electrolyze water to generate a gas comprising hydrogen. The integrated passageway device includes an upper cover and a lower cover. The upper cover and the lower cover are combined to form a condensing passageway, a humidifying passageway and an output passageway, respectively. The lower cover is one-peace structure and has a condensing passageway inlet and an outlet coupled to each other by the condensing passageway, a humidifying passageway inlet and a humidifying passageway outlet coupled to each other by the humidifying passageway, and an output passageway inlet and an output passageway outlet coupled to each other by the output passageway. The output passageway outlet is coupled to the external environment and the condensing passageway inlet is coupled to the water tank to receive the gas comprising hydrogen. The humidifying module is coupled to the lower cover respectively coupled to the condensing passageway outlet and the condensing passageway inlet. The humidifying module has a humidifying chamber configured to humidify the gas comprising hydrogen and transfer it to the humidification passageway. The hydrogen water module is configured to a accommodate liquid and has an input structure coupled with lower cover and the humidifying passageway outlet in order to transport the gas comprising hydrogen to the liquid configured to generate a hydrogen liquid. The hydrogen water module another comprises an output structure which coupled to output passageway inlet configured to output a gas comprising hydrogen.

Wherein, the humidifying module is disposed in the integrated passageway device and water tank. The humidifying module further has a communicating chamber which couples condensing passageway inlet of integrated passageway device and the refrigerator. The electrolytic module is accommodated in the water tank, and to electrolyze the water to be electrolyzed to generate the gas comprising hydrogen into the water tank. The gas comprising hydrogen flows to the integrated passageway device through communicating chamber. The communicating chamber doesn't communicate with the humidifying chamber.

Wherein, the integrated hydrogen gas generator of the hydrogen water module further comprises the gas baffle plate assembly in communicating chamber. The gas baffle plate assembly can reduce or avoid water or electrolytes in the gas comprising hydrogen, which flows to the gas baffle plate assembly, from entering the condensing passageway.

Wherein, the upper cover further has a first cap fixed at a position of the upper cover which is above and corresponding to the position of the humidifying passageway outlet. The first cap movably covers the humidifying passageway outlet. The upper cover can selectively allow the gas comprising hydrogen to flow out of the humidifying passageway outlet or to block water and water vapor from flowing out of the humidifying passageway outlet.

Wherein, the integrated hydrogen gas generator of the hydrogen water module further comprises a filter couple to the lower cover. The filter can be used to filter impurities from the gas comprising hydrogen. The lower cover also has a filtering inlet and filtering outlet coupled to filter. The output passageway is divided into a first section passageway and a second section passageway. The first section passageway is coupled to the output passageway inlet and the filtering inlet to input the gas comprising hydrogen into the filter. The second section passageway is coupled to the filtering outlet and the output passageway outlet to output the filtered gas comprising hydrogen from the filter.

Wherein, the upper cover further has a second cap which is fixed at a position of the upper cover which is above and corresponding to the position of the filtering inlet. The second cap movably covers the filtering inlet to selectively allow the gas comprising hydrogen to flow into the filtering inlet or to block water and water vapor from flowing into the filtering inlet.

Wherein, the humidifying module is disposed between the integrated passageway and the filter. The humidifying module has an input column and an output column. The input column can be coupled to the filtering inlet of the lower cover of the integrated passageway module and the filter. The output column can be coupled to the filter outlet of the lower cover of the integrated passageway module and the filter. The input column and output column doesn't communicate with the humidifying chamber.

Wherein, the integrated hydrogen gas generator of hydrogen water module further comprises a nebulizer coupled to the lower cover. The nebulizer has a nebulizer inlet and a nebulizer outlet, wherein the nebulizer inlet is coupled with the output passageway to receive the gas comprising hydrogen and nebulizer inlet is coupled with the external environment. The nebulizer can also generate atomized gas to be mixed with the gas comprising hydrogen to form a healthy gas, and then output the healthy gas to the external environment by the nebulizer outlet.

Wherein, the surface of the humidifying module is further recessed inward to form a nebulizer accommodating chamber to accommodate the nebulizer.

Wherein, the hydrogen water module further comprises a water input/output structure, a grip part and a telescopic buckle. The water input/output structure can selectively provide a water input channel to allow water to be inputted to the hydrogen water module or to allow the hydrogen liquid to be outputted and output passageway configured to inject water in hydrogen water module or output the hydrogen liquid. The grip part can be disposed on one side of water hydrogen module away from the humidifying module, and the grip part comprises a linkage button. The telescopic buckle is coupled with the linkage button, and it is configured to selectively couple the hydrogen water module and humidifying passageway.

Wherein, the integrated hydrogen gas generator of the hydrogen water module further comprises a transfer valve disposed between the humidifying passageway and the output passageway. When the linkage button drives the telescopic buckle, the hydrogen water module is decoupled from the humidifying passageway and the output passageway, and the humidifying passageway and the output passageway being coupled to each other through the transfer valve.

Wherein, the integrated hydrogen gas generator further comprises a bubbled stick disposed in humidifying module of humidifying chamber. The bubbled stick can be coupled with the humidifying chamber and the condensing passageway, so as to refine the gas comprising hydrogen from the condensing passageway to evenly distribute the gas comprising hydrogen in the humidifying chamber.

In another embodiment, an integrated hydrogen gas generator with a water hydrogen module of the present invention comprises a water tank, an electrolytic module, an integrated passageway module, a condensation body, a humidifying module and a hydrogen water module. The water tank is configured to accommodated electrolyte water. The electrolytic module is configured to electrolyze the electrolyte water to generate a gas comprising hydrogen. The integrated passageway device includes an upper cover and lower cover, wherein the upper cover and lower cover are combined to each other to form a condensing space, a humidifying passageway and output passageway. The lower cover is an integrated structure. The lower cover has a condensing passageway inlet and a condensing passageway outlet coupled to the condensing space, a humidifying inlet and a humidifying outlet coupled to the humidifying passageway, and an output passageway inlet and an output passageway outlet coupled to the output passageway. The output passageway outlet is coupled to the external environment, and the condensing passageway inlet is coupled to the water tank to receive the gas comprising hydrogen. The condensation body is coupled to the upper cover and is accommodated in condensing space. The condensation body and the upper cover are combined to each other to form a condenser with condensing space, and the condensing passageway inlet is coupled to condensing passageway outlet configured to condense a gas comprising hydrogen in condensing passageway. The humidifying module is coupled to lower cover to be coupled with the condensing passageway outlet and the humidifying passageway inlet respectively, so as to humidify the gas comprising hydrogen and transfer the humidified gas comprising hydrogen to the humidifying passageway. The hydrogen water module can be configured to accommodate liquid. The hydrogen water module comprises an input structure coupled with the lower cover and the humidifying passageway outlet to input the gas comprising hydrogen into the liquid for generation the liquid comprising hydrogen. The hydrogen water module further comprises an output structure coupled to the output passageway outlet to output the gas comprising hydrogen.

Compared to the prior art, the integrated hydrogen gas generator with the hydrogen water module of the present invention has the following advantage:

1. The integrated hydrogen gas generator with hydrogen water module of the present invention has the condensation, humidification and the electrolysis devices vertically stacked with each other, and connects each of the said devices by an integrated passageway module to allow the integrated hydrogen gas generator operating without additional piping to each of the said device. Therefore, the problems of the cumbersome assembly process of the generator, complicated wiring, large volume of the generator, and dropping, gas leakage, and water leakage problems of the pipeline can be avoided.

2. In addition to the water electrolyzing function, the integrated hydrogen gas generator with hydrogen water module of the present invention further comprises a hydrogen water module to contain the liquid to produce a hydrogen liquid, so as to achieve two different functions in one machine.

3. Because the water electrolyzed by the electrolytic module is not the liquid in the hydrogen water module and the hydrogen liquid in the hydrogen water module is formed by inputting the gas comprising hydrogen into the hydrogen water module, the liquid contained in the hydrogen water module can be any liquid, so as to improve the motive for the users to drink the hydrogen liquid.

BRIEF DESCRIPTION OF THE APPENDED DRAWINGS

Some of the embodiments will be described in detail, with reference to the following figures, wherein like designations denote like members, wherein:

FIG. 3b is an explosion diagram of according to FIG. 3a.

FIG. 3c is an explosion diagram illustrating a part of the integrated gas generator with a hydrogen water module in FIG. 3a.

DETAILED DESCRIPTION OF THE INVENTION

In order to make advantages, spirit and character of the present invention more easily, it will be described and discussed in detail by reference attached figure with embodiment. It is worth nothing that theses embodiment only replaced of the invention. But it can be implemented in many different forms and is not limited to the embodiments which described in this specification. In contrast, these embodiments are provided to make the public content of the present invention more thorough and comprehensive.

The terminology used in the in the description of the present invention is for the purpose of describing particular embodiments only and does not limit the public embodiments of the present invention. So the singular form also includes the plural form unless the context clearly indicates. Unless otherwise defined, all terminology which used in the present specification (included technical and scientific terminology) has the same meanings of the present each public embodiment which ordinary technician can comprehend. The above terminology will be described as the identical meaning of the same field in technology and it will not be explained as ideal meaning or too official meaning, besides it is clearly limited in each embodiments of the present public invention.

In the description of the present specification, the terminologies "in an embodiment", "in another embodiment" means that the specific feature, structure, material or characteristic of the present embodiment is involved in at least one embodiment of the present invention. In the description of the present specification, the schematic representation of the mentioned terminologies does not necessarily refer to the same embodiment.

Furthermore, the described specific feature, structure, material or characteristic can be involved in any one or more embodiments in a proper way.

In the description of the present invention, unless otherwise specified or limited, the terms "initial connection", "connection", and "setting" should be interpreted in a broad meaning. Such as it can be mechanical or electrical connection, it can also be the internal connection of two elements, it can be directly connected, and it can also be indirectly connected through an intermediate medium. For those of ordinary technician in the art, the specific meanings of the above terms can be understood according to specific circumstances.

Figure 1:
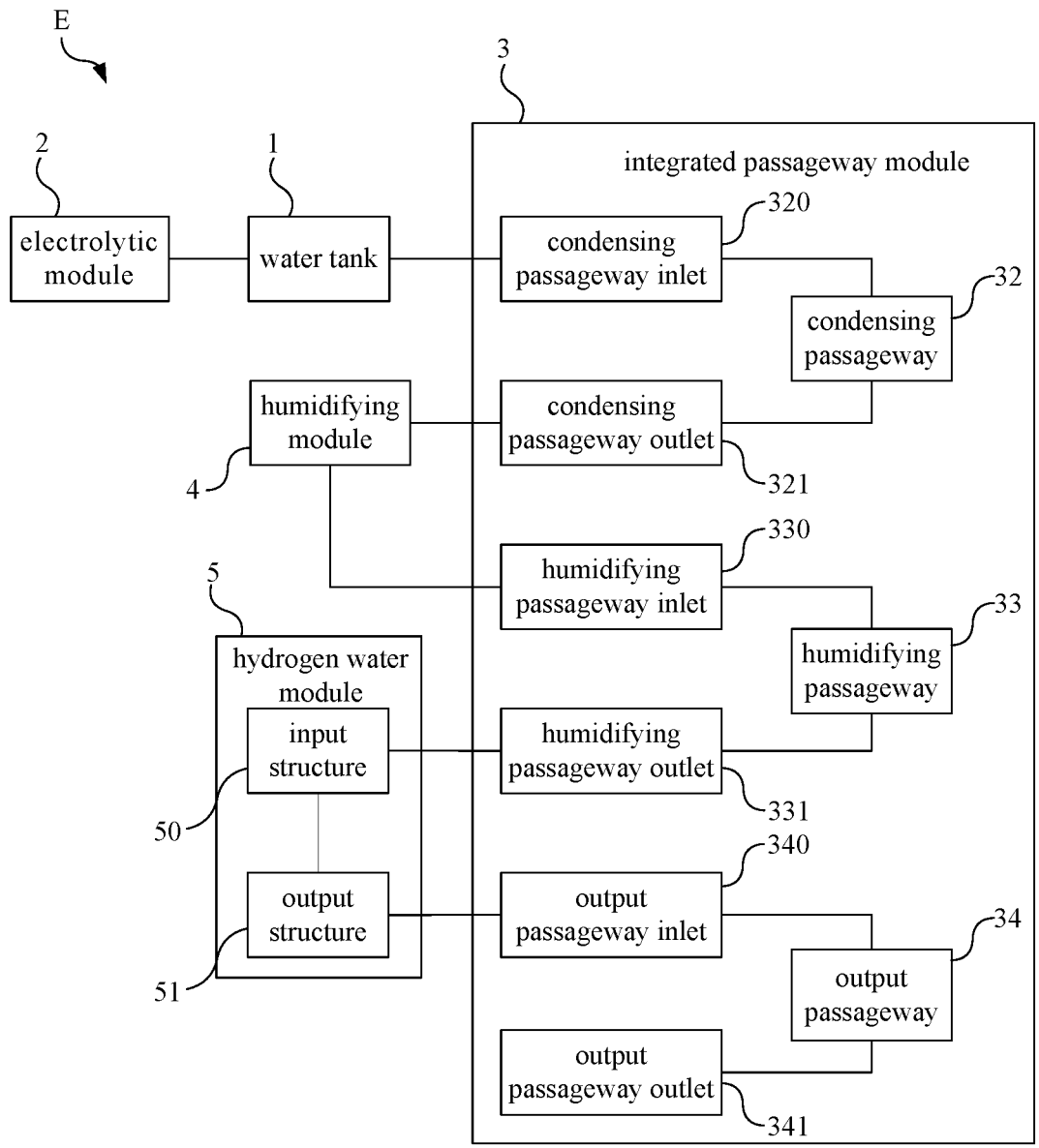
FIG. 1 is a function block diagram illustrating an integrated gas generator with a hydrogen water module according to an embodiment of the present invention.
Figure 2:
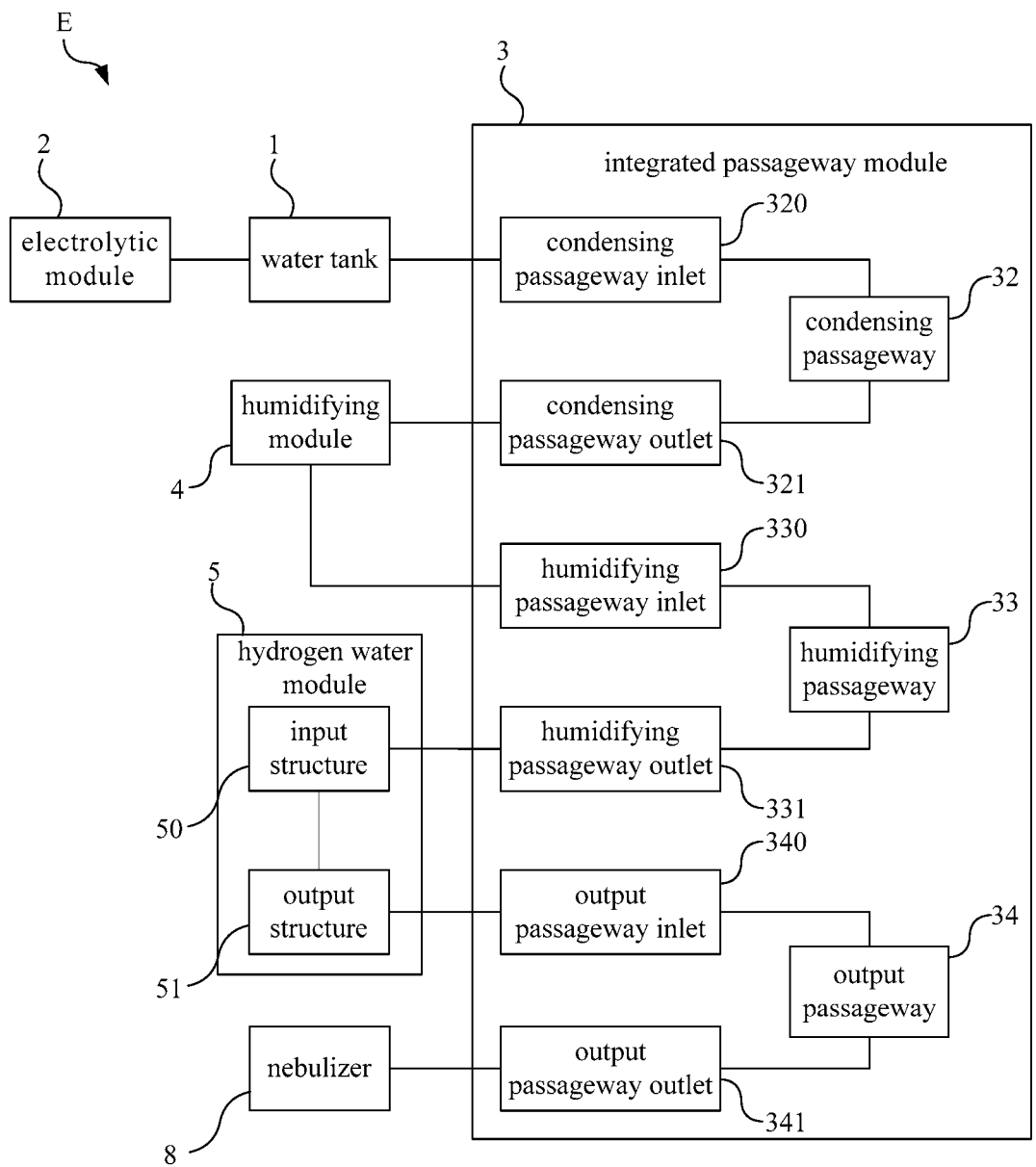
FIG. 2 is a further function block diagram according to FIG. 1.
Figure 3A:
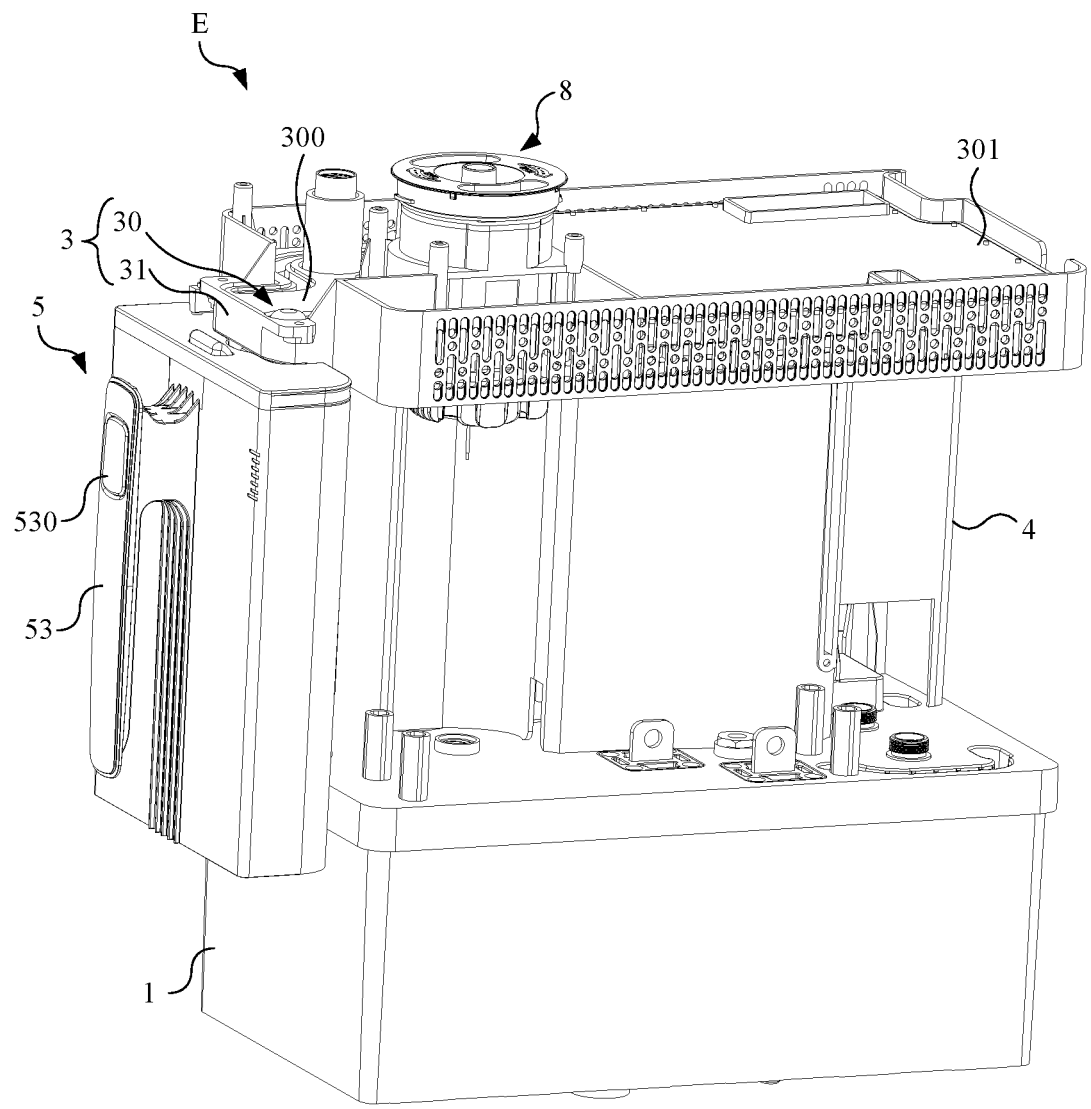
FIG. 3a is a structural diagram illustrating an integrated gas generator with a hydrogen water module according to an embodiment of the present invention.
Figure 3B:
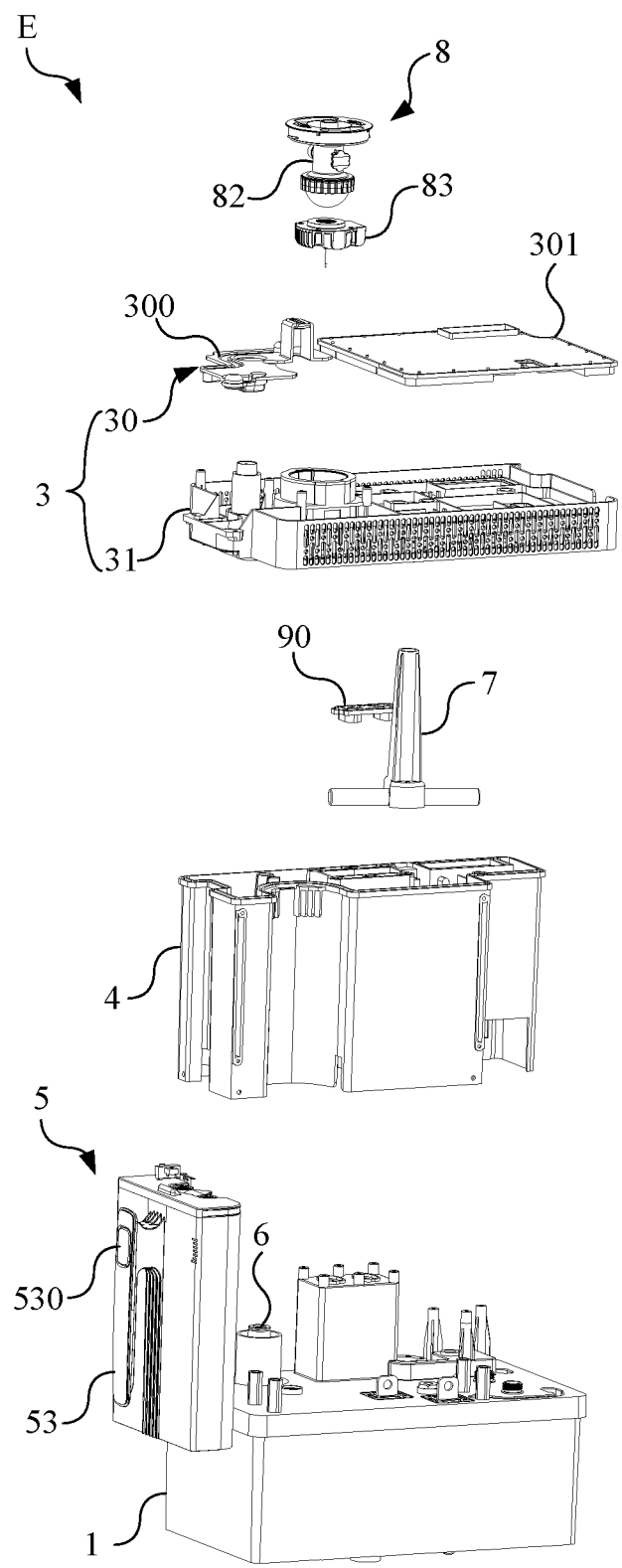
Figure 3C:
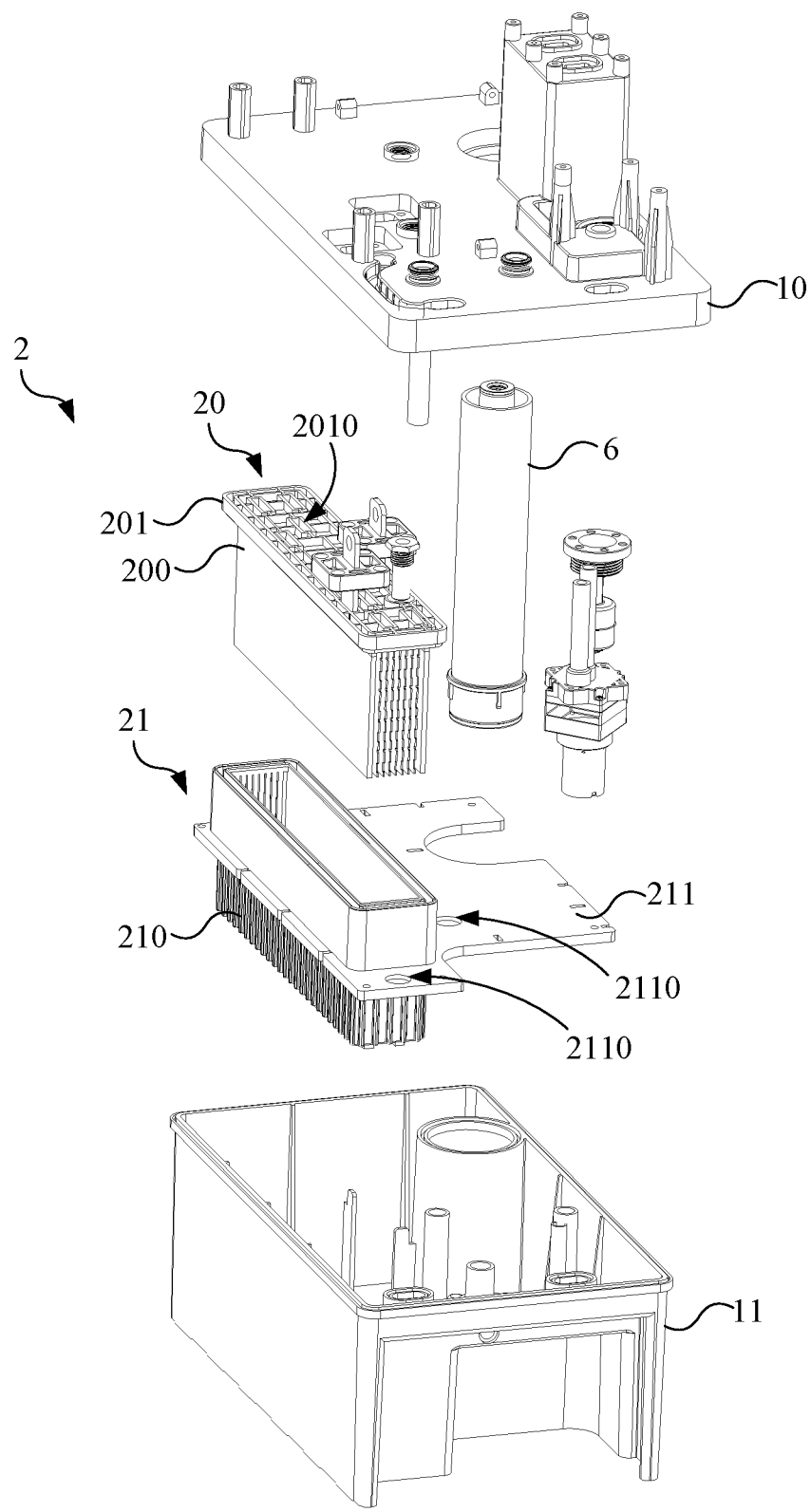
Figure 3D:
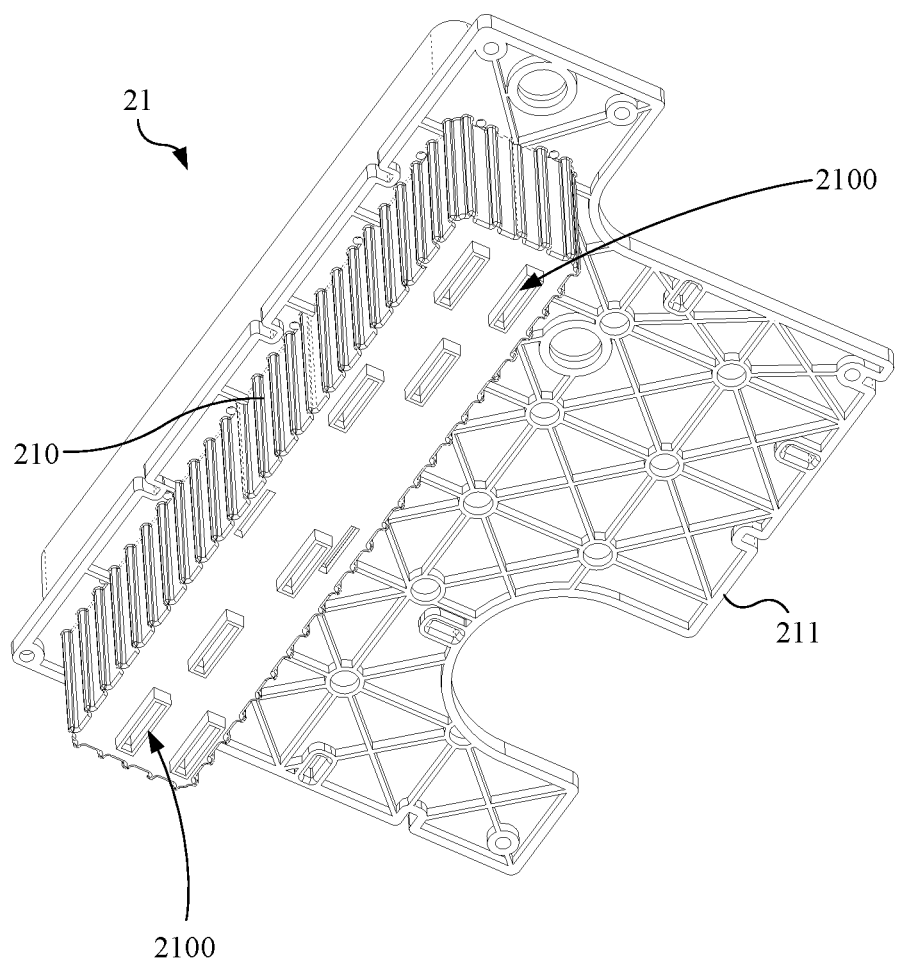
FIG. 3d is a bottom view diagram illustrating of the electrolytic module fixed plate in FIG. 3c.
Figure 4:
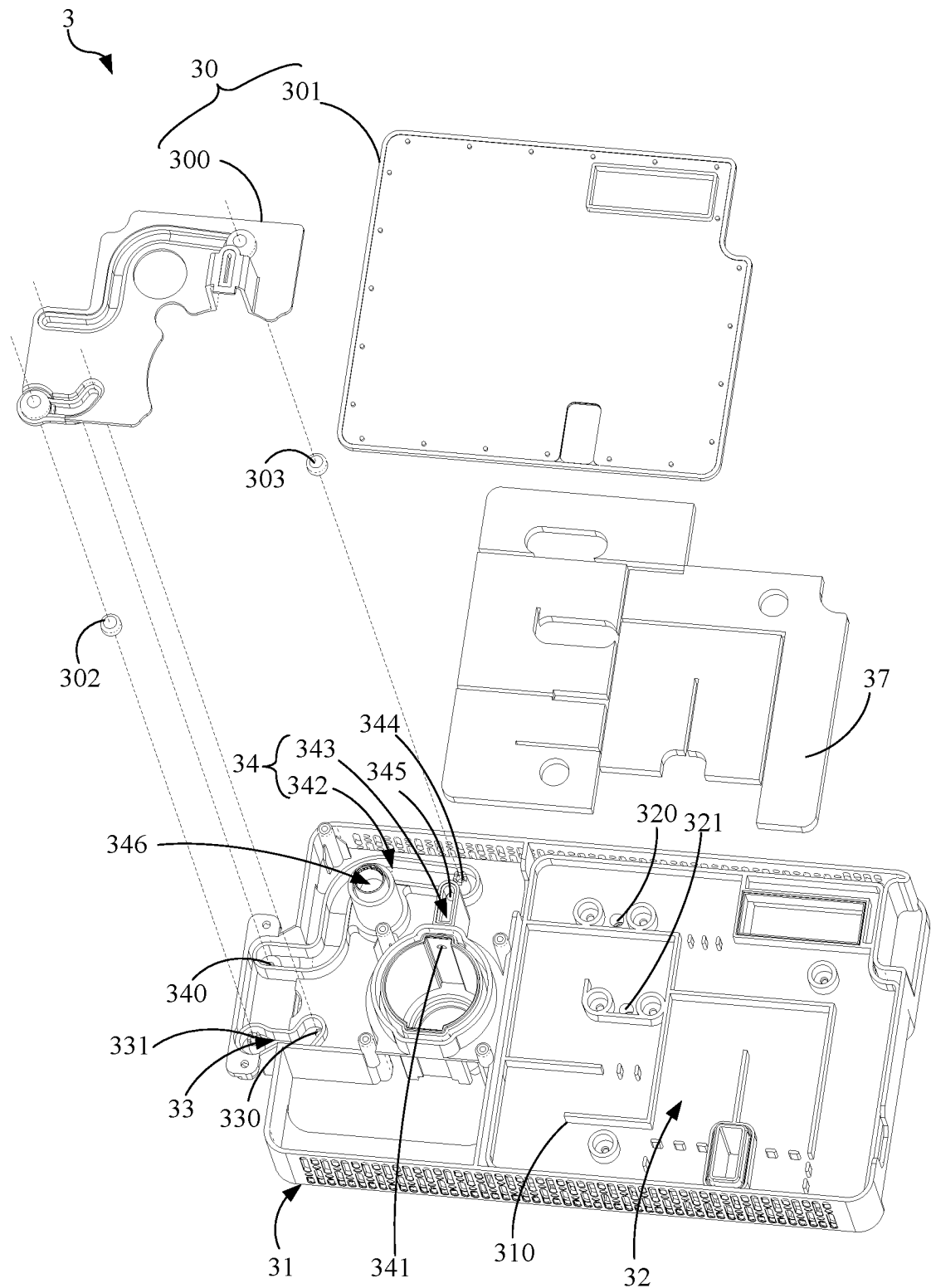
FIG. 4 is an explosion diagram illustrating the integrated passageway devices of the integrated hydrogen gas generator with the hydrogen water module according to an embodiment of the present invention.

Please refer to FIG. 1 to FIG. 4. FIG. 1 is a function block diagram illustrating an integrated hydrogen gas generator E with a hydrogen water module according to an embodiment of the present invention. FIG. 2 is a further function block diagram according to FIG. 1. FIG. 3a is structural diagram illustrating the integrated hydrogen gas generator E with the hydrogen water module according to an embodiment of the present invention. FIG. 3b is an explosion diagram of FIG. 3a. FIG. 4 is an explosion diagram illustrating the integrated passageway devices 3 of the integrated hydrogen gas generator E with the hydrogen water module according to an embodiment of the present invention. As shown in FIG. 1, FIG. 3 and FIG. 4, the present invention provided an integrated hydrogen gas generator E with the hydrogen water module which comprises a water tank 1, an electrolytic module 2, an integrated passageway device 3, a humidifying module 4, and a hydrogen water module 5. The water tank 1 is configured to accommodate electrolyte water. The electrolytic module 2 can be disposed in the water tank 1 to electrolyze the electrolyte water in the water tank 1 to generate a gas comprising hydrogen. As shown in FIG. 3 and FIG. 4, the integrated passageway device 3 includes an upper cover 30 and a lower cover 31. The upper cover 30 and the lower cover 31 are combined to form a condensing passageway 32, a humidifying passageway 33, and an output passageway 34, respectively, and the lower cover 31 is formed integrally. Wherein, the lower cover 31 has a condensing passageway inlet 320 and a condensing passageway outlet 321 coupled with the condensing passageway 32, a humidifying passageway inlet 330 and a humidifying passageway outlet 331 coupled to the humidifying passageway 33, and an output passageway inlet 340 and an output passageway outlet 341 coupled to the output passageway 34. The output passageway outlet 341 is coupled to the external environment, and the condensing passageway inlet 340 is coupled to the water tank 1 to receive the gas comprising hydrogen generated by the electrolytic module 2 in the water tank 1. The humidifying module 4 is coupled to the lower cover 31 to communicate with the condensing passageway outlet 321 and the humidifying passageway inlet 330, respectively. The humidifying module 4 is configured to humidify the gas comprising hydrogen and deliver it to the humidifying passageway 33. The hydrogen water module 5 is configured to accommodate a liquid. The hydrogen water module 5 includes an input structure 50 coupled to the lower cover 31 and connected to the humidifying passageway outlet 331 to input the gas comprising hydrogen into the liquid to generate a hydrogen liquid. The hydrogen water module 5 further includes an output structure 51 connected to the output passageway inlet 340 to output the gas comprising hydrogen. In this embodiment, as shown in FIG. 2, the integrated hydrogen gas generator E with the hydrogen water module of the present invention can further include a nebulizer 8 coupled to the output passageway outlet 341 to provide an atomized gas.

Please refer to FIG. 3a, FIG. 3b, FIG. 3c and FIG. 3d. FIG. 3c is an explosion diagram illustrating a part of the integrated gas generator with a hydrogen water module in FIG. 3a, and FIG. 3d is a bottom view diagram illustrating of the electrolytic module fixed plate in FIG. 3c. In an embodiment, as shown in FIG. 3c, the water tank 1 can include a cover body 10 and a tank body 11, the tank body 11 is configured to accommodate electrolyte water, and the cover body 10 can cover the water tank body 11. The electrolytic module 2 can be disposed in the water tank 1. The electrolytic module 2 includes an electrode plate assembly 20 and an electrolytic module fixing plate 21. The electrode plate assembly 20 can be disposed in the electrolytic module body 210 of the electrolytic module fixing plate 21. The electrode plate assembly 20 includes a plurality of electrode plates 200 and a plurality of pad 201 connected to the electrode plates 200 respectively. Each of the pads 201 is disposed on the upper surface of each electrode plate 200, so that the electrode plates 200 are spaced from each other. The electrode plate assembly 20 can be disposed in the electrolytic module body 210 to form to a plurality of electrode channels. As shown in 3c and 3d, in another embodiment, the electrolytic module fixing plate 21 includes an electrolytic module body 210 and a partitioning plate 211. The partitioning plate 211 can be used to fix the electrolytic module 2 in the water tank 1, and the water tank 1 can be divided into an upper part and a lower part. The electrolyzed water is mainly located in the lower part, and the gas comprising hydrogen, which is generated by electrolysis, it is mainly located in the upper part. In order to keep the upper and lower parts still in circulation, the partition plate 211 has a plurality of circulation holes 2110 to communicate the upper part with the lower part. As shown in FIG. 3d, the electrolytic module body 210 has a plurality of water flow holes 2100 on the bottom thereof, so that the electrolyte water can flow into each electrode flow channel from the water flow holes 2100, and each electrode plate 200 can electrolyze water to generate the gas comprising hydrogen. In addition, the pads 201 can also have a plurality of gas flow holes 2010, so that the gas comprising hydrogen generated by electrolysis can flow into the water tank 1 through the gas flow holes 2010. The electrolytic module fixing plate 21 can be formed integrally. In addition, it can be understood that those skilled in the art can be design the shape of the partitioning plate 211 according to the requirements to provide a space for disposing other components.

Figure 5:
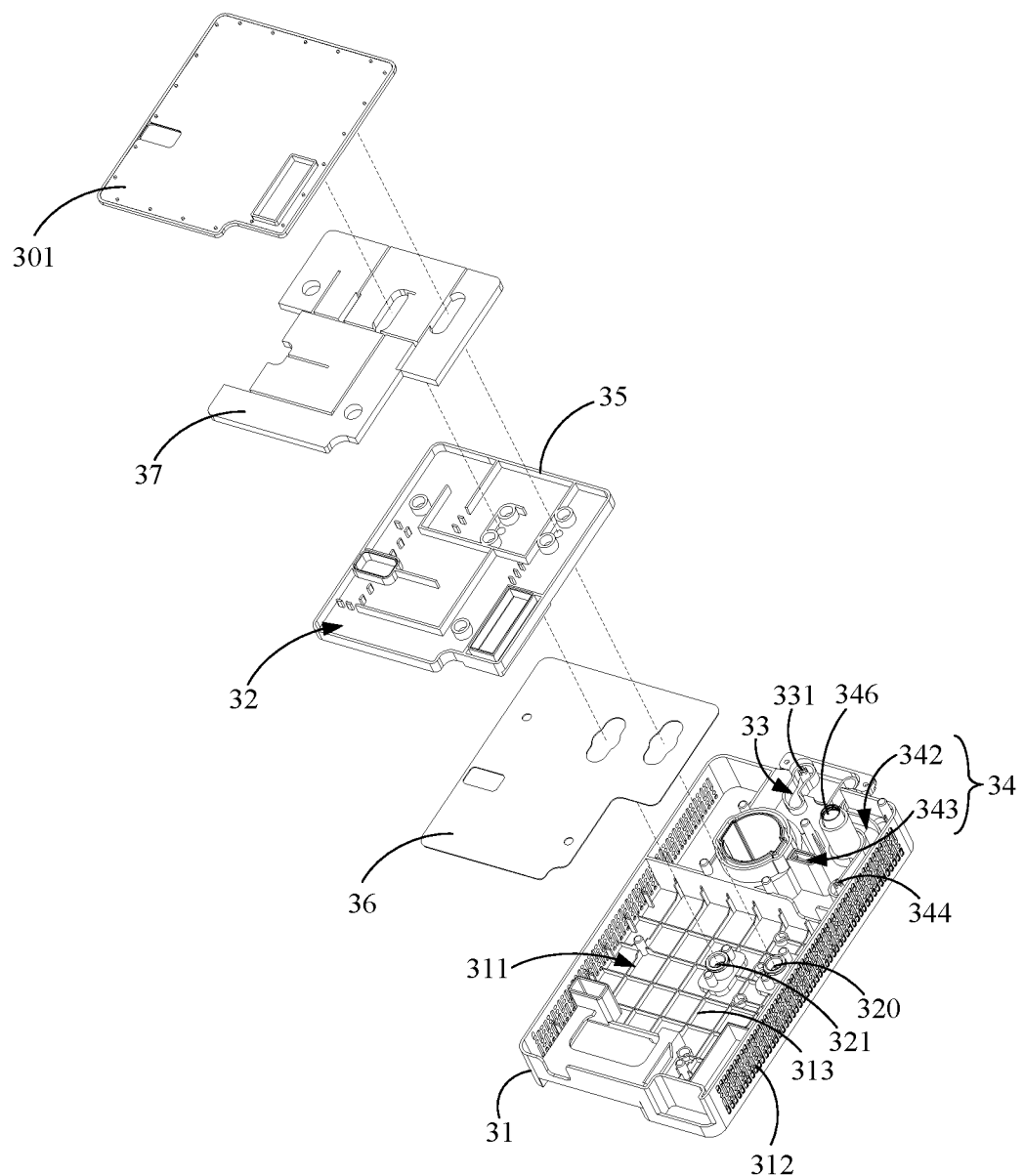
FIG. 5 is an explosion diagram illustrating the integrated passageway devices of the integrated hydrogen gas generator with the hydrogen water module according to another embodiment of the present invention.

In practice applications, the condensing passageway 32 can be formed in two ways. Please refer to FIG. 4 and FIG. 5. FIG. 5 is an explosion diagram illustrating the integrated passageway devices 3 of the integrated hydrogen gas generator E with the hydrogen water module according to another embodiment of the present invention. One of the forming method ways of condensing passageway 32 is that: the upper cover 30 can include a first upper cover 300 and a second upper cover 301. The first upper cover 300 and the lower cover 31 can form the humidifying passageway 33 and the output passageway 34. The lower cover 31 has a plurality of spacer plates 310 in a specific arrangement. The second upper cover 301 is combined with the lower cover 31 to form the condensing passageway 32. Wherein, the integrated hydrogen gas generator E of with the hydrogen water module of the present invention further has a plurality of filtering material 37. The filtering cotton materials 37 may can be disposed in the condensing passageway 32 to configure to initially filter initially the impurities in the gas comprising hydrogen. Wherein, the aforementioned spacer plates 310 can be used to separate a plurality of filtering materials 37 to prevent the filtering materials 37 from overlapping with each other or prevent them from contacting each other and absorbing moisture from each other to reduce the effect of condensation and moisture absorption.

As shown in FIG. 5, another ways for forming the condensing passageway 32 of the present invention is that: the lower cover 31 is combined with the second upper cover 301 to form a condensing space 311 first. The integrated hydrogen gas generator E with a hydrogen water cup module further includes a condensing body 35 coupled to the above of the second upper cover 301 and accommodated disposed in the condensing space 311. The condensing body 35 is combined with the second upper cover 301 to form a condenser with the condensing passageway 32, and the condensing passageway 32 is coupled to the condensing passageway inlet 320 and the condensing passageway outlet 321 of the lower cover 31 to condense the gas comprising hydrogen which flows into the condensing passageway 32 from the condensing passageway inlet 320. The integrated hydrogen gas generator E with the hydrogen water module of the present invention further includes a condensing plate 36 and the filtering materials 37. The condensing plate 36 is disposed between the condensing body 35 and the lower cover 31 and configured to enhance the condensation effect of the condenser. The filtering materials 37 can be disposed in the condensing passageway 32 to initially filter the impurities in the gas comprising hydrogen. In order to enhance the condensation effect, the lower side cover 31 has a plurality of ventilation structures 312 which can be the vents on the side of the lower side cover 31, and has a padding structure 313 in the condensing space 311.

When the second upper cover 301 with the condensing body 35 is combined with the lower cover 31, a gap between the condensing plate 36 and the lower cover 31 is generated by the padding structure 313. When the integrated hydrogen gas generator E with the hydrogen water module of the present invention is operating, a fan can be configured in the integrated hydrogen gas generator E with a the hydrogen water module to generate a condensing flow in the integrated hydrogen gas generator E, and the condensing flow passes through the ventilation structures 312 and the gap created by the uplift padding structure 313 of the lower cover 31 to enhance the condensing effect of the condenser.

Figure 6:
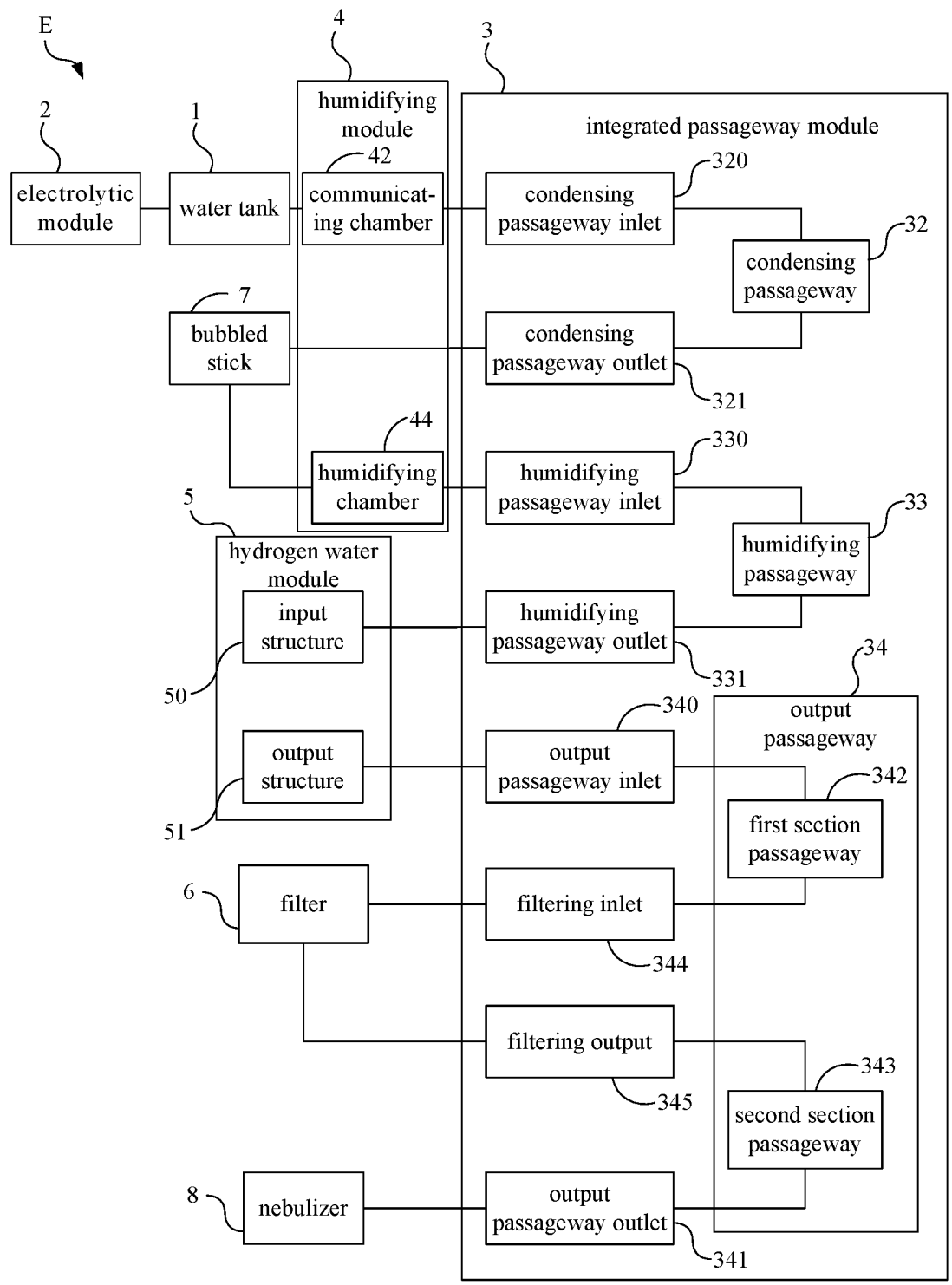
FIG. 6 is a function block diagram illustrating the integrated hydrogen gas generator with the hydrogen water module according to another embodiment of the present invention.

Please refer to FIG. 6 in combination. FIG. 6 is a functional block diagram illustrating the integrated hydrogen gas generator E with the hydrogen water module according to another embodiment of the present invention. In practice applications, the integrated hydrogen gas generator E with the hydrogen water module further includes a filter 6 coupled to the lower cover 31 to filter the impurities in the gas comprising hydrogen. The lower cover 31 further has a filtering inlet 344 and a filtering outlet 345 to be coupled to the filter 6. The output passageway 34 is divided into a first section passageway 342 and a second section passageway 343. The first section passageway 342 communicates the output passageway inlet 340 and the filtering inlet 344 to input the gas comprising hydrogen into the filter 6, and the second section passageway 343 communicates the filtering outlet 345 and the output passageway outlet 341 to output the gas comprising hydrogen from the filter 6.

Before the further descriptions for the humidifying module 4, it should be noted that the integrated hydrogen gas generator E with the hydrogen water module of the present invention can further include a bubbled stick 7 and the nebulizer 8. The condensing passageway 32 can be coupled to the humidifying module 4 through the condensing passageway outlet 321 and the bubbled stick 7, so as to allow the condensed gas comprising hydrogen to flow from the condensing passageway 32 into the humidifying module 4. The nebulizer 8 is coupled to the lower covers 31. The nebulizer 8 is configured to atomize the liquid to be atomized therein to form an atomizing gas, and to mix the atomizing gas with the gas comprising hydrogen to form a healthy gas.

Figure 7:
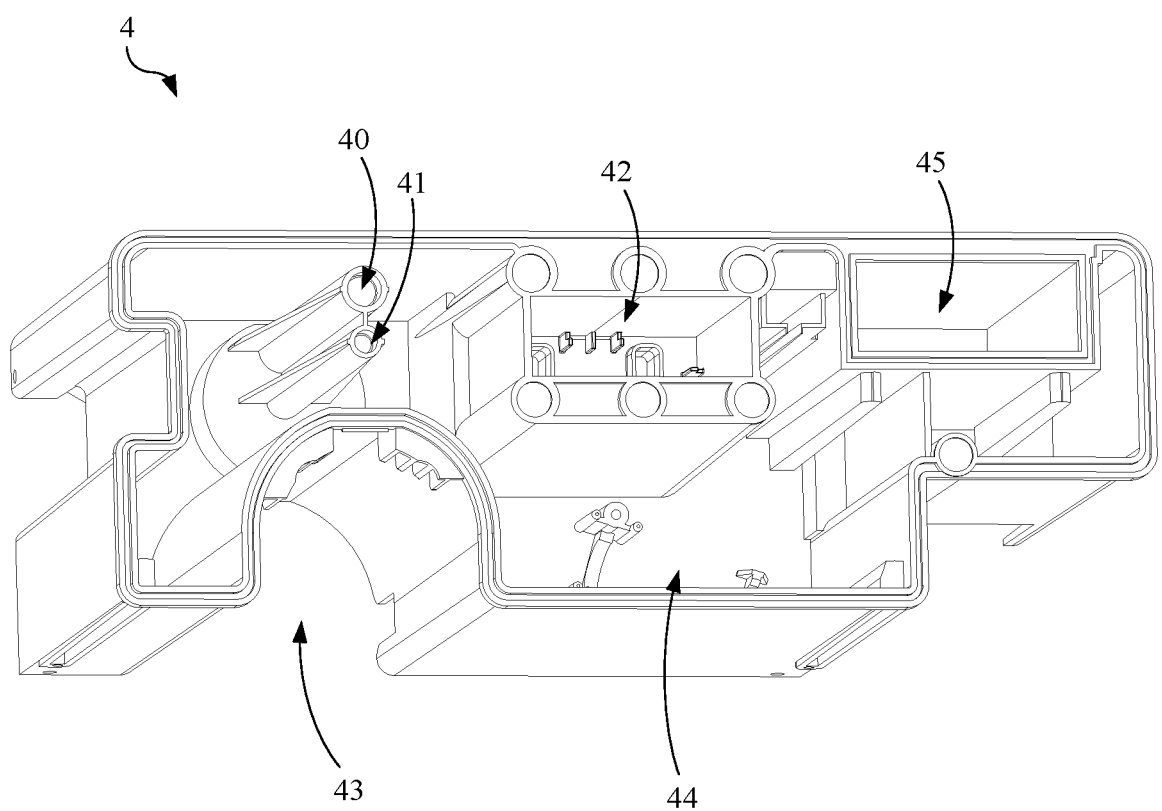
FIG. 7 is a structural diagram illustrating the humidifying module in FIG. 3.
Figure 8:
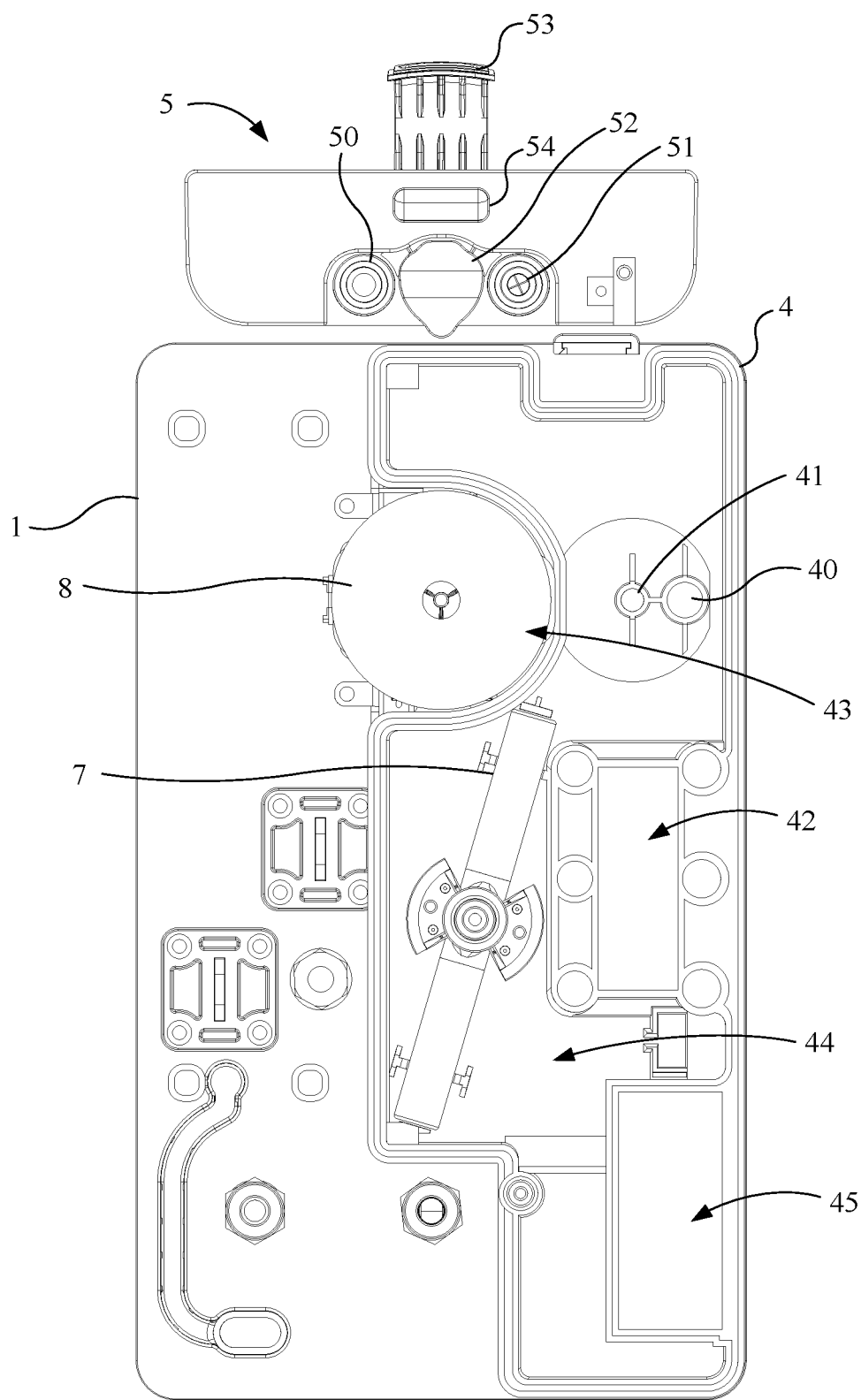
FIG. 8 is a configuration diagram illustrating the internal configuration of the humidifying module in FIG. 3.

Please refer to FIG. 4, FIG. 7 and FIG. 8 together. FIG. 7 is a diagram illustrating the structure of the humidifying module 4 of FIG. 3. FIG. 8 is a diagram illustrating the configuration in the humidifying module 4 of FIG. 3. The humidifying module 4 is configured to connect between the integrated passageway device 3 and the water tank 1. The humidifying module 4 has an input column 40 and an output column 41 for connecting the integrated passageway device 3 with the filter 6, a communicating chamber 42 for connecting the integrated passageway device 3 and the water tank 1, a nebulizer accommodating chamber 43 for accommodating the nebulizer 8, a humidifying chamber 44 for accommodating the bubbled stick 7 and water to be electrolyzed, and the circuit room 45 accommodating the circuit equipment. Wherein, in an embodiment, the input column 40, the output column 41 and the communicating chamber 42 are not connected with the humidifying chamber 44. The nebulizer accommodating chamber 43 is further formed by the surface of the humidifying module 4 depressing inward. The filter 6 is coupled to the lower cover 31 through the input column 40 and the output column 41 of the humidifying module 4. In addition, the lower cover 31 further includes a water injection passageway 346 for connecting the humidifying chamber 44 of the humidifying module 4 and the external environment. Water can be inputted to the humidifying module 4 through the water injection passageway 346 for humidifying. Furthermore, the aforementioned units in the humidifying module 4 can be formed integrally.

Figure 9:
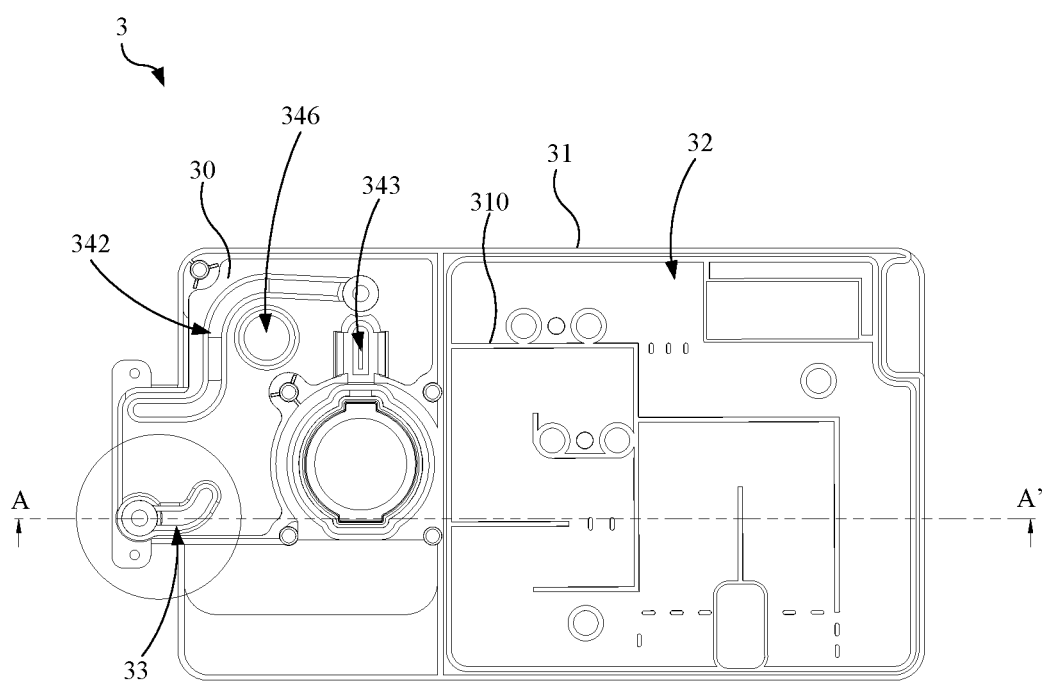
FIG. 9 is a top view diagram illustrating the integrated passageway device of the integrated hydrogen gas generator with the hydrogen water module according to an embodiment of the present invention.
Figure 10:
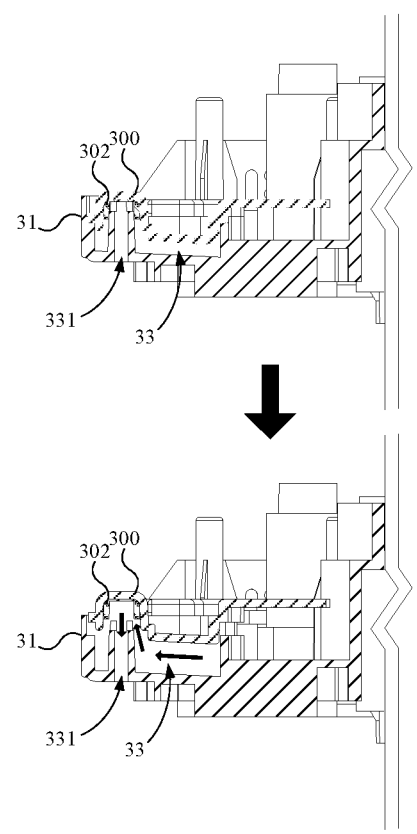
FIG. 10 is a sectional view diagram for the operation of the part along the A-A' section line shown in FIG. 9.

To further describe the operation of the integrated passageway device 3, please refer to FIG. 9 and FIG. 10. FIG. 9 is a top view diagram illustrating the integrated passageway device 3 of the integrated hydrogen gas generator E with the hydrogen water module according to an embodiment of the present invention. FIG. 10 is a partial cross-sectional view diagram of the operation diagram according to along the A-A' section line shown in FIG. 9. In order to more clearly describe the operation mode between the upper cover 30 and the lower cover 31 of the integrated passageway device 3, the second section upper cover 301 is omitted in the figure to clearly show the internal structure. Taking the humidifying passageway 33 as an example, the humidifying passageway 33 circled in FIG. 9 is shown in a cross-section diagram by along the A-A' section line. As shown in FIG. 10, the upper cover 30 of the integrated passageway device 3 further has a first cap 302, which is disposed at a position of the upper cover 30 above the humidifying passageway outlet 331 and movably covers on the humidifying passageway outlet 331. The upper cover 30 is configured to selectively allow the gas comprising hydrogen to flow out of the humidifying passageway outlet 331 or block water and water vapor from flowing out of the humidifying passageway outlet 331. In detail, when the gas comprising hydrogen does not entered the integrated passageway device 3 yet, the upper cover 30 abuts above the lower cover 31 to block the water and water vapor from flowing out of the humidifying passageway outlet 331 from the humidifying passageway 33. Wherein, the first cap 302 block the water and water vapor by the water-sealing effect which is generated by the water with the capillary phenomenon in the gap between the first cap 302 and the humidifying passageway outlet 331, or by pressing the upper cover 30 on the humidifying passageway outlet 331 by gravity. When the gas comprising hydrogen enters the integrated passageway device 3, the upper cover 30 is pushed up by the gas comprising hydrogen. At this time, the gap between the first cap 302 and the humidifying passageway inlet 331 is formed by pushing the upper cover 30 upward, and then the gas comprising hydrogen of the humidifying passageway 33 can flow out from the humidifying passageway outlet 331. In addition to the first cap 302, the upper cover 30 further has a second cap 303, which is fixed at a position of the upper cover 30 above the filtering inlet 344 to movably cover the filtering inlet 344, so as to selectively allow the gas comprising hydrogen to flow to the filtering inlet 344 or block the water and the water vapor from flowing to the filtering inlet 344, as the operation of the first cap 302. The water in the integrated hydrogen gas generator E with the hydrogen water module would be prevented from flowing out of humidifying passageway outlet 331 and the filtering inlet 344 into hydrogen water module 5 and the filter 6 when shaking or tilting by the first cap 302 and the second cap 303, so as to reduce the possibility of contamination in the hydrogen water module 5 or damage to other mechanical components in the integrated hydrogen gas generator E due to water ingress.

Please refer to FIG. 10, the humidifying passageway 33 is designed as tilted, and the part of the humidifying passageway 33 near the humidifying passageway outlet 331 is higher and the part of the humidifying passageway 33 far away from at the humidifying passageway outlet 331 is lower. The tilted design allowing the water and the water vapor in the humidifying passageway 33 to return to the humidifying passageway inlet 330 and further into the humidifying module 4 configured to prevent water and water vapor flow into humidifying passageway outlet 331, and only make the gas comprising hydrogen of humidifying passageway 33 flows into the humidifying passageway outlet 331. In addition, the output passageway 34 also has the same tilted design. The part of the output passageway 34 near the filtering inlet 344 is higher than the part of the output passageway 34 away from filtering inlet 344, so as to prevent water and moisture from flowing into the filtering inlet 344.

Figure 11:
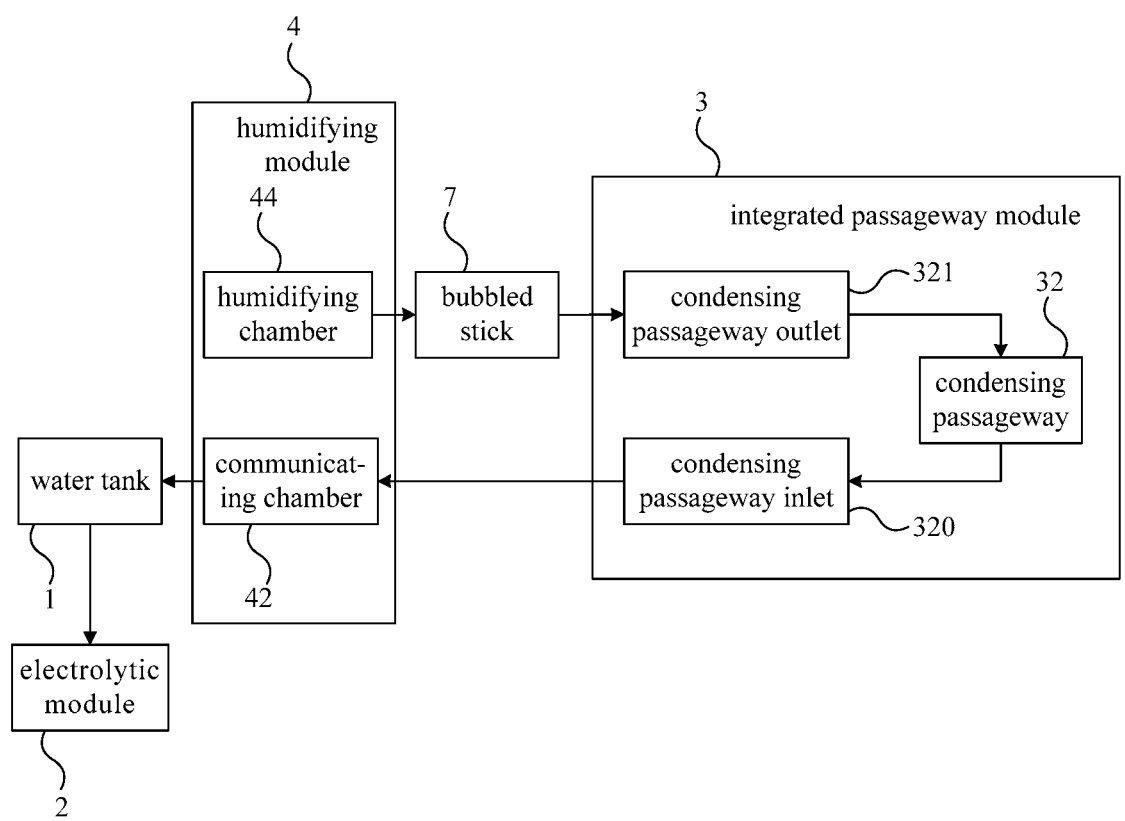
FIG. 11 is a function block diagram illustrating the water path of the integrated hydrogen gas generator with the hydrogen water module according to an embodiment of the present invention.

The operation of the integrated hydrogen gas generator E with the hydrogen water module in regard to the water path and the gas path according to an embodiment of the present invention will be described as following. Please refer to FIG. 11. FIG. 11 is a function block diagram illustrating the integrated hydrogen gas generator E with the hydrogen water module according to an embodiment of the present invention. In the water path, the water is inputted to humidifying module 4 from the external environment through the inputting passageway 346, and then vacuum pump is utilized to extract gas from the water tank 1 and the communicating chamber 42 to form a negative pressure. The condensing passageway 32 and the humidifying module 4 are connected to communicating chamber 42, so that the pressure difference makes the water of humidifying module 4 to flow into the communicating chamber 42 in the water tank 1 through the condensing passageway 32. In practice, the humidifying module 4 has a bubbled stick 7 disposed therein to connect humidifying module 4 and condensing passageway 32. Therefore, when the vacuum pump extracts gas, the water of humidifying module 4 will flow through the bubbled stick 7 into the integrated passageway device 3 from the condensing passageway outlet 321, and then flow into the water tank 1 through the communicating chamber 42 and the condensing passageway inlet 320. In another embodiment, the integrated hydrogen gas generator E further includes a water pump which is disposed in the humidifying chamber 44 of the humidifying module 4, so that it directly presses the water accommodated in the humidifying chamber 44 to allow water to enter the water tank 1 through the bubbled stick 7, the condensing passageway outlet 32, the integrated passageway device 3, the condensing passageway inlet 320, and the communicating chamber 42. This water will be electrolyzed by the electrolytic module 2 to generate the gas comprising hydrogen. In other words, the water in the humidifying module 4 can be used not only for humidifying comprising hydrogen gas, but also used as the water to be electrolyzed.

Figure 12:
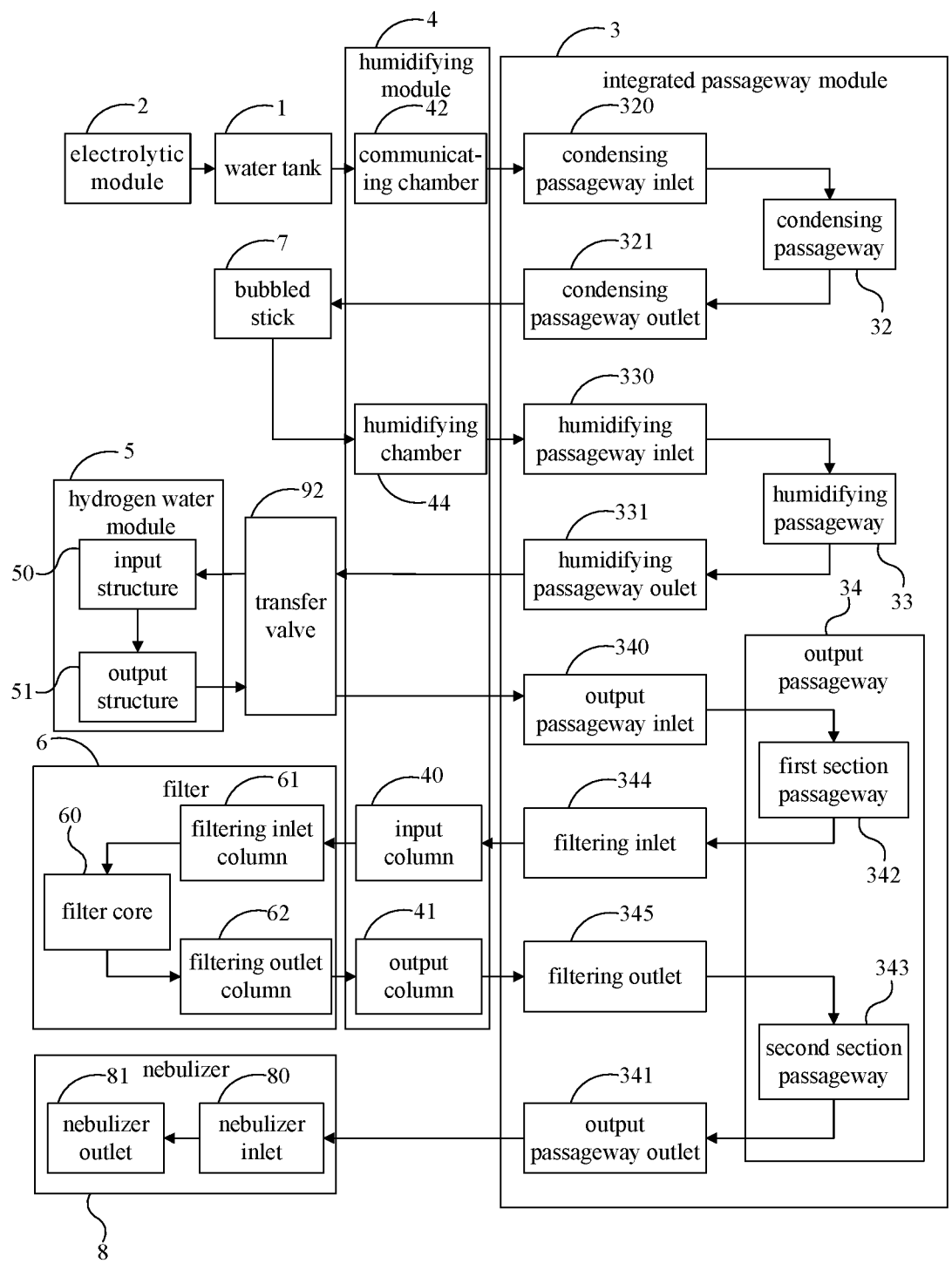
FIG. 12 is a function block diagram illustrating the gas path of the integrated hydrogen gas generator with the hydrogen water module according to an embodiment of the present invention.
Figure 13:
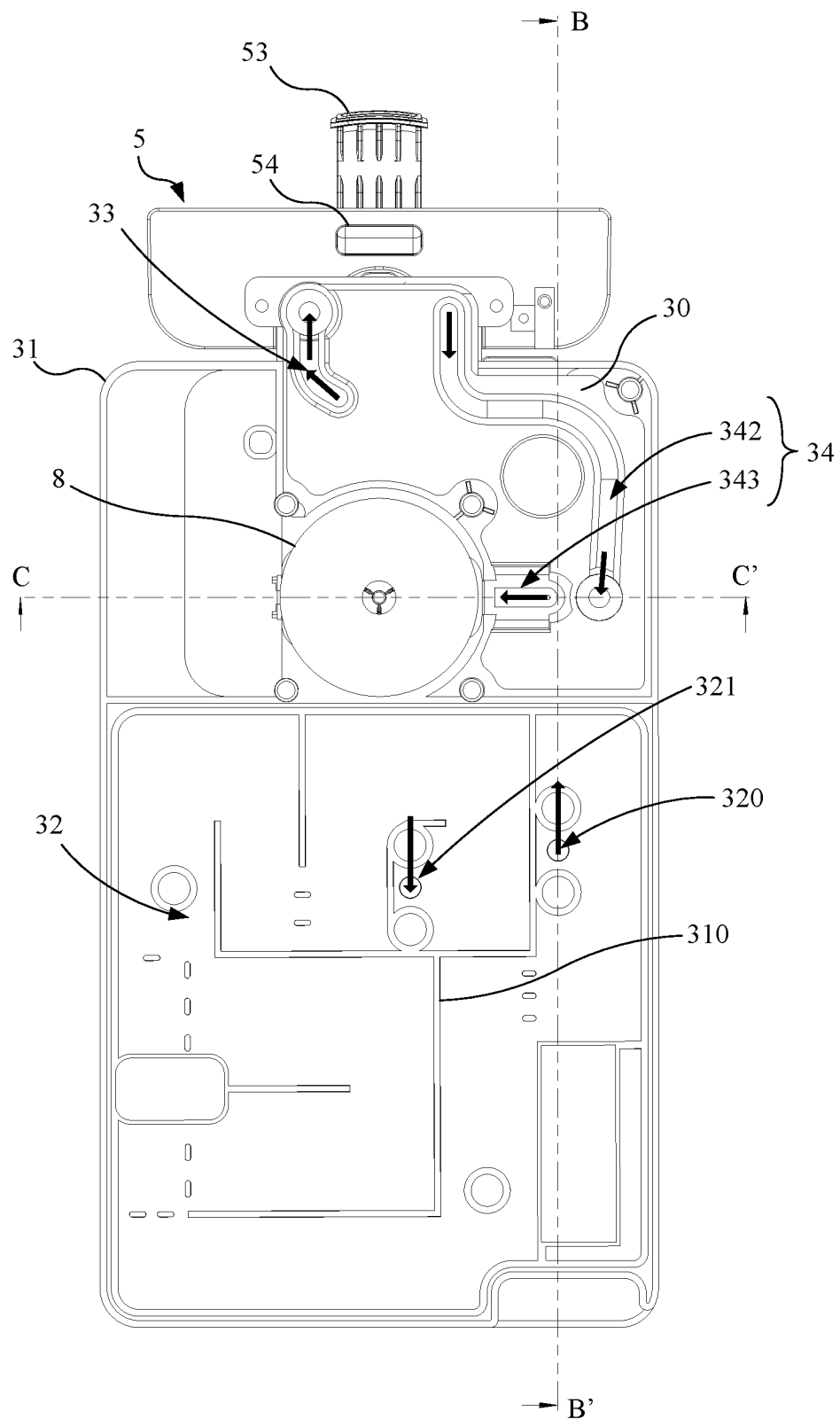
FIG. 13 is a top view diagram illustrating the water tank, the first upper cover, the lower cover, the nebulizer, the hydrogen water module of the integrated gas generator with a hydrogen water module according to an embodiment of the present invention.
Figure 14:
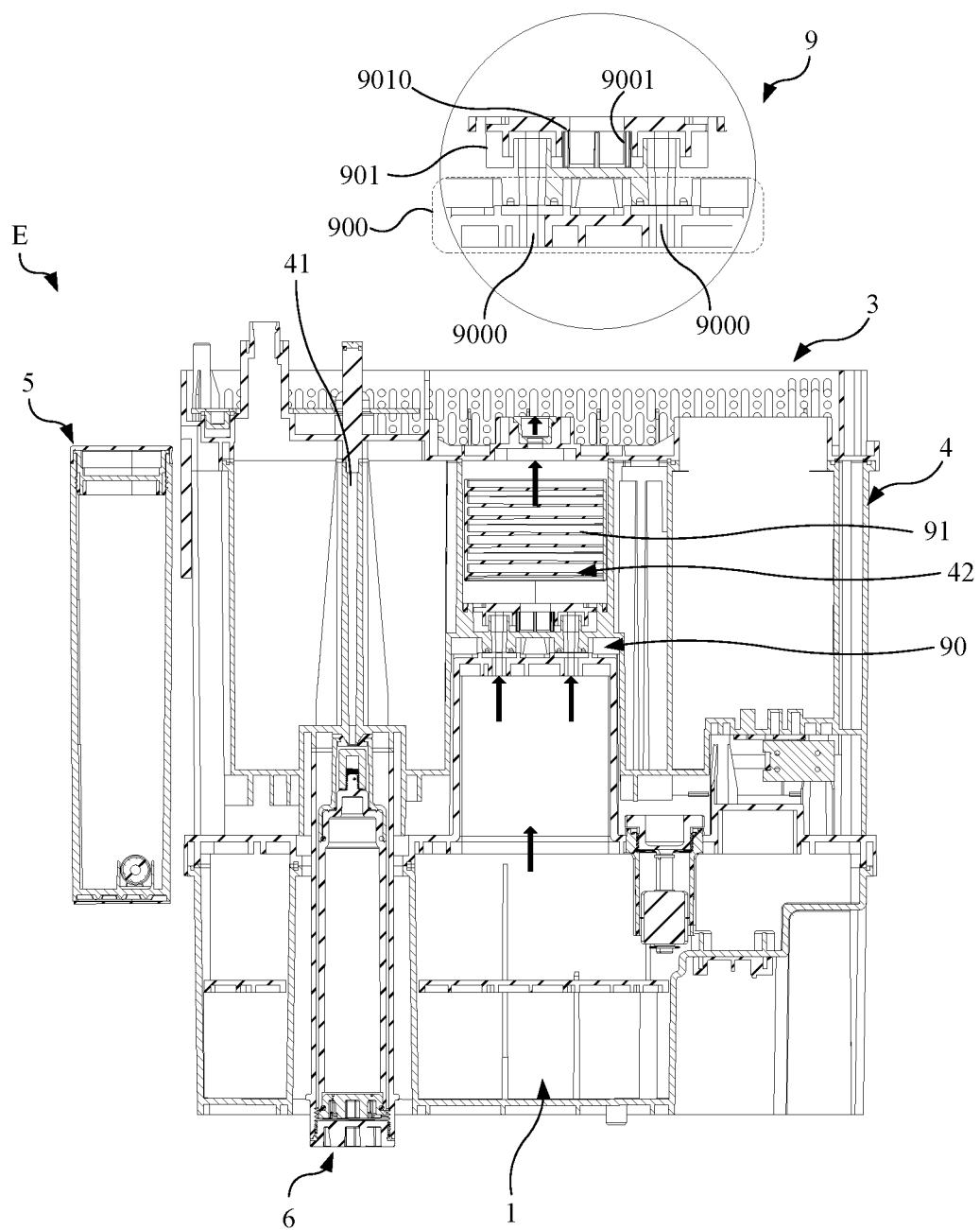
FIG. 14 is a sectional diagram illustrating the integrated hydrogen gas generator along the B-B' section line in FIG. 13.
Figure 15:
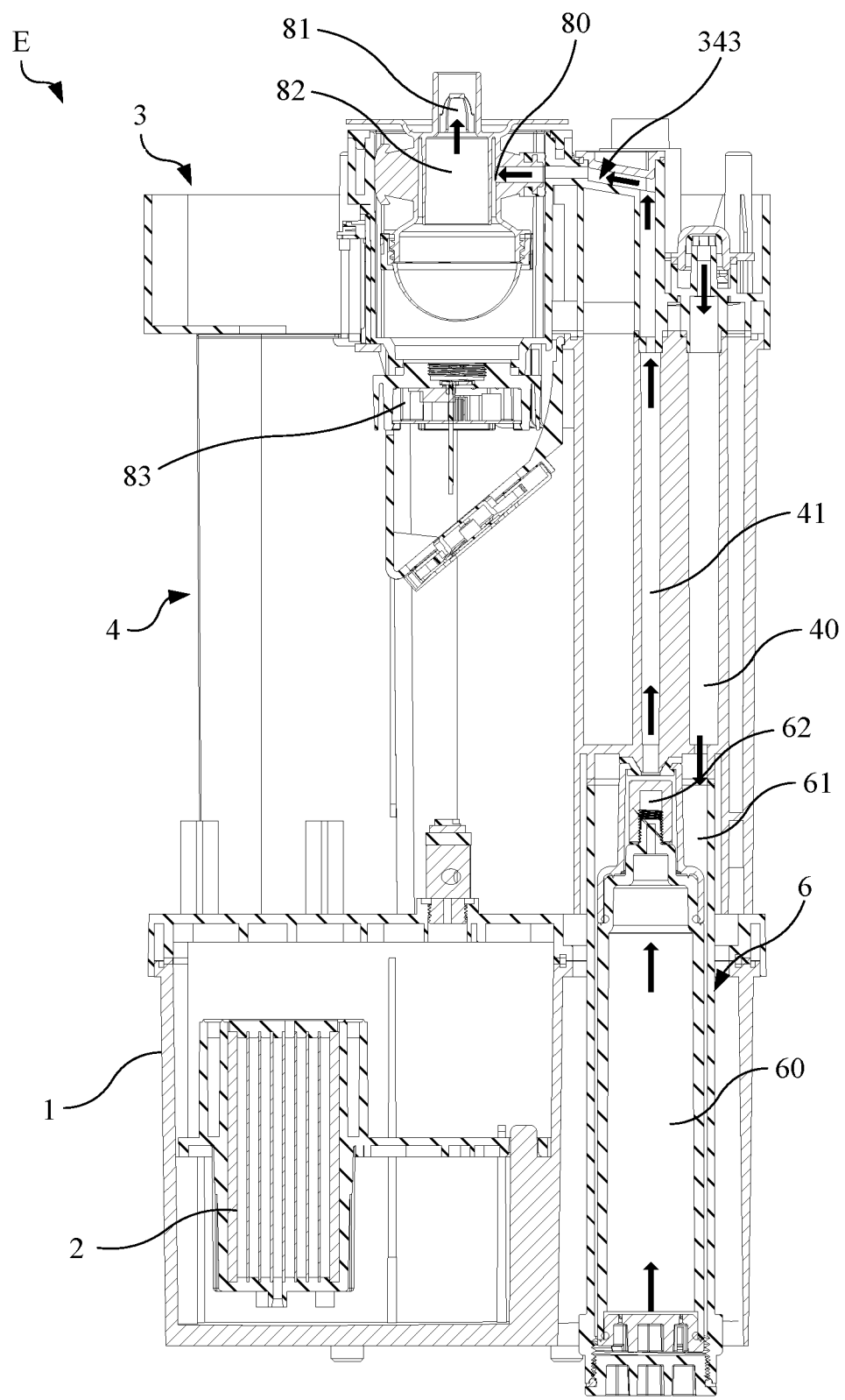
FIG. 15 is a sectional diagram illustrating the integrated hydrogen gas generator along the C-C' section line in FIG. 13.

Please refer FIG. 12 to FIG. 15. FIG. 12 is a function block diagram illustrating the gas path of the integrated hydrogen gas generator E with the hydrogen water module according to an embodiment of the present invention. FIG. 13 is a top view diagram illustrating the water tank, the first upper cover, the lower cover, the nebulizer, and the hydrogen water module of the integrated hydrogen gas generator E with the hydrogen water module according to an embodiment of the present invention. FIG. 14 is a sectional diagram illustrating the integrated hydrogen gas generator E along the B-B' section line in FIG. 13. FIG. 15 is a sectional diagram illustrating the integrated hydrogen gas generator E along the C-C' section line in FIG. 13. The gas path comprises condensation, humidification, and filtering and atomizer stages. As shown in FIG. 12 to FIG. 15, the arrows illustrate the flow directions of the gas comprising hydrogen. The electrolytic module 2 is disposed in water tank 1 to electrolyze the electrolyte water to form a gas comprising hydrogen in water tank 1. The gas comprising hydrogen flows through the communicating chamber 42 and from the condensing passageway inlet 320 into the condensing passageway 32 of integrated passageway device 3 to be condensed (as show in FIG. 14). The condensed gas comprising hydrogen flows from condensing passageway outlet 321 through the bubbled stick 7 to the humidifying chamber 44 in the humidifying module 4 to be humidified. The humidified gas comprising hydrogen flows through the humidifying passageway inlet 330 into the humidifying passageway 33 of integrated passageway device 3, and then from the humidifying passageway outlet 331 into the hydrogen water module 5 to be mixed with the liquid in the hydrogen water module 5 to form a liquid comprising hydrogen. Then, as shown in FIG. 12, the extra gas comprising hydrogen in the hydrogen water module 5 enters the first section passageway 342 of the output passageway 34 from the output passageway inlet 340, and then flows from the filtering inlet 344 through the input column 40 into the filter 6 to be filtered. The filtered gas comprising hydrogen flows from the filtering outlet 345 through the input column 41 into the second passageway of the output passageway 34, and then flows through the output passageway outlet 341 into the nebulizer 8 to be outputted to the external environment after mixing with the atomized gas.

For a detailed description of the communicating chamber 42, please refer to FIGS. 11, 12 and 14. The integrated hydrogen gas generator E with the hydrogen water module further includes a water blocking device 90 and a gas baffle plate assembly 91, both of which can be disposed in the communicating chamber 42. As shown in FIG. 14, the water blocking device 90 is disposed above the water tank 1 to block the electrolyzed water of the water tank 1 from flowing out when the water tank 1 is inclined at an inclined angle. In practice, the water blocking device 90 includes a bottom 900 (as shown in the dotted line) and a water-proof component 901. The bottom 900 has an air inlet 9000 and an elastic plug 9001. The air inlet 9000 is configured to receive the gas comprising hydrogen. The water-proof component 901 has a plug hole 9010, and the elastic plug 9001 is provided on the plug hole 9010 in a recoverable manner, and the air inlet 9000 is kept open by leaning against the water-proof component 901. When the water tank 1 or the integrated hydrogen gas generator E with the hydrogen water module is inclined at an inclined angle, the elastic plug 9001 is compressed and then slides into the plug hole 9010 to couple the water-proof member 901 with the bottom 900, thereby closing the air inlet 9000 to block the flow of electrolyzed water from water tank 1.

The air baffle plate assembly 91 is disposed above the water blocking device 90. The air baffle plate assembly 91 is configured to decrease or prevent the water vapor and electrolytes of the gas comprising hydrogen from flowing into the condensing passageway 32. The air baffle plate assembly 91 includes a plurality of boards staggered with each other.

Furthermore, the water vapor and electrolytes in the gas comprising hydrogen will be condensed on the air baffle plate assembly 91 due to the obstruction of the air baffle plate assembly 9, when the gas comprising hydrogen flows through the communicating chamber 42. The water vapor and the electrolyte condensed on the air baffle plate assembly 91 can be flushed back to the water tank 1 by the water from the integrated passageway device 3 driven by the pump, so as to maintain the electrolyte concentration in the electrolyzed water and further maintain the electrolysis efficiency.

Please refer FIG. 12 and FIG. 15. The filter 6 includes a filter core 60, a filtering inlet column 61 and a filtering outlet column 62. The filter core 60 is configured to filter the impurities in the gas comprising hydrogen, and the filtering inlet column 61 and the filtering outlet column 62 are respectively connected with two sides of the filter core 60. The filtering inlet column 61 can be connected to the filtering inlet 344 through the input column 40 of humidifying module 4. The filtering outlet column 62 can be connected to the filtering outlet 345 through the output column 41 of humidifying module 4. Wherein, the gas comprising hydrogen flows into the filtering inlet column 61 through the filtering inlet 344, and then enters the filter core 60 through filtering inlet column 61 to be filtered. The filtered gas comprising hydrogen flows into the filtering outlet column 62 from the filter core 60, and then the filtering outlet column 62 outputs the gas comprising hydrogen through the filtering outlet 345. As shown in FIG. 15, the configuration of the filter 6 of the present invention is that the filtering inlet column 61 and the filtering outlet column 62 are located on the same side of the filter 6. The filter core 60 of the integrated hydrogen generator E can be easily renewed from bottom in this configuration to simplify the complex processes for renewing the filter core.

The nebulizer 8 has an atomizing inlet 80 and an atomizing outlet 81. The nebulizer inlet 80 is connected to the output passageway outlet 341 and the output passageway 34 to receive the gas comprising hydrogen, and the nebulizer output 81 is connected to the external environment. Wherein, the nebulizer 8 further includes a mixing chamber 82 and an oscillator 83, the mixing chamber 82 is configured to carry the precursor to be atomized therein and to mix the atomized gas with the gas comprising hydrogen to form a health-care gas. The oscillator 83 is disposed below the mixing chamber 82 to oscillate and atomize the precursor to the required atomizing gas. The atomized gas includes at least one of water vapor, atomizing potion and volatile essential oil.

Figure 16:
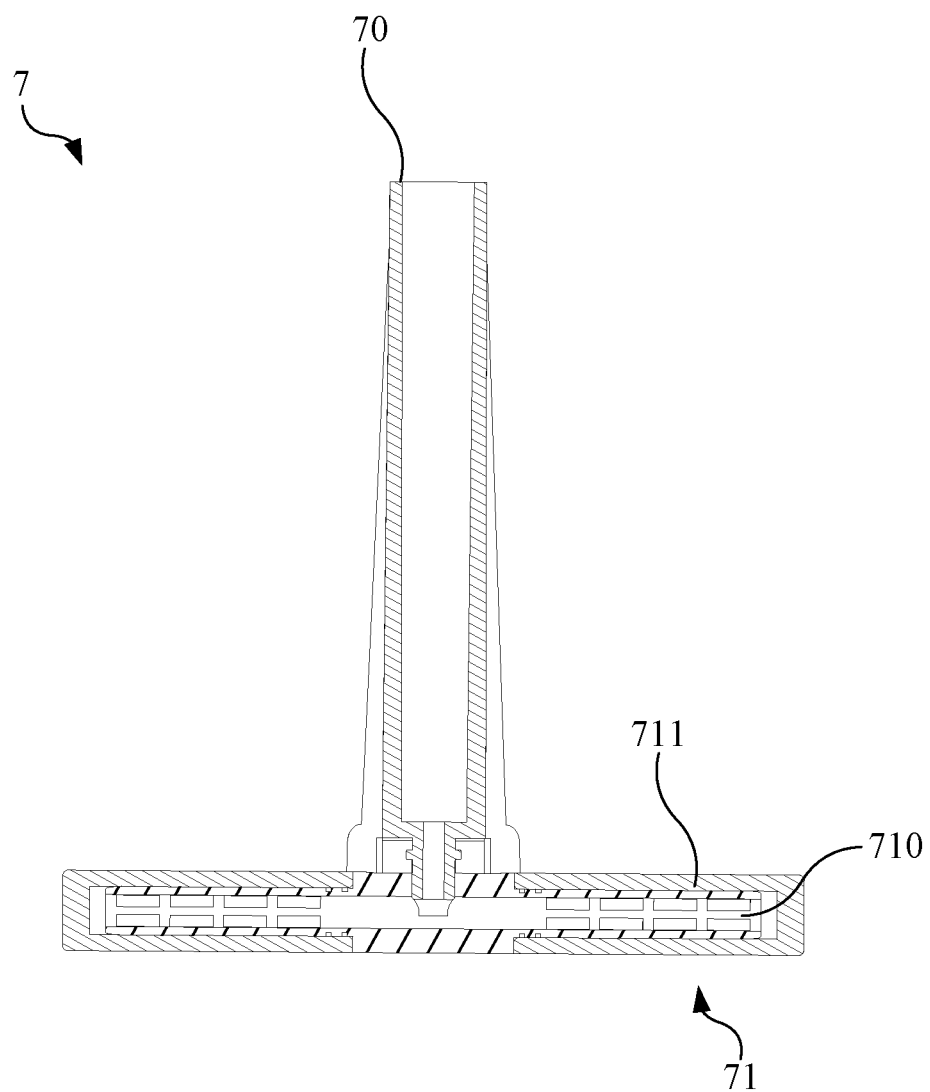
FIG. 16 is the sectional diagram of the bubbled stick of the integrated hydrogen gas generator with the hydrogen water module according to an embodiment of the present invention.

The followings are the detailed descriptions of the bubbled stick 7. Please refer FIG. 11, FIG. 12 and FIG. 16. FIG. 16 is a sectional diagram of the bubbled stick 7 of the integrated hydrogen gas generator with the hydrogen water module according to an embodiment of the present invention. The bubbled stick 7 can be coupled to the humidifying module 4 and the condensing passageway 32 of the integrated passageway device 3 to refine the gas comprising hydrogen flowing from the condensing passageway 32, so that the gas comprising hydrogen can be evenly distributed into the humidifying passageway 4. As shown in FIG. 16, the bubbled stick 7 includes a cylinder 70 and a rod 71. The cylinder 70 is a hollow structure, and the rod 71 has at least one branch column 710 and a porous coating layer 711 covering the branch column 710. In practice, the rod 71 of the bubbled stick 7 is immersed in the water of the humidifying module 4. The gas comprising hydrogen can enter the bubbled stick 7 from the rod 71 and flow to the humidifying module 4, so as to be humidified by the water in the humidifying module 4. In addition, the water in humidifying module 4 can enter the rod 71 through the porous coating layer 711, and flow into the rod cylinder 70 from the rod 71, so that the water in the humidifying module 4 can flow out of the humidifying module 4.

Figure 17:
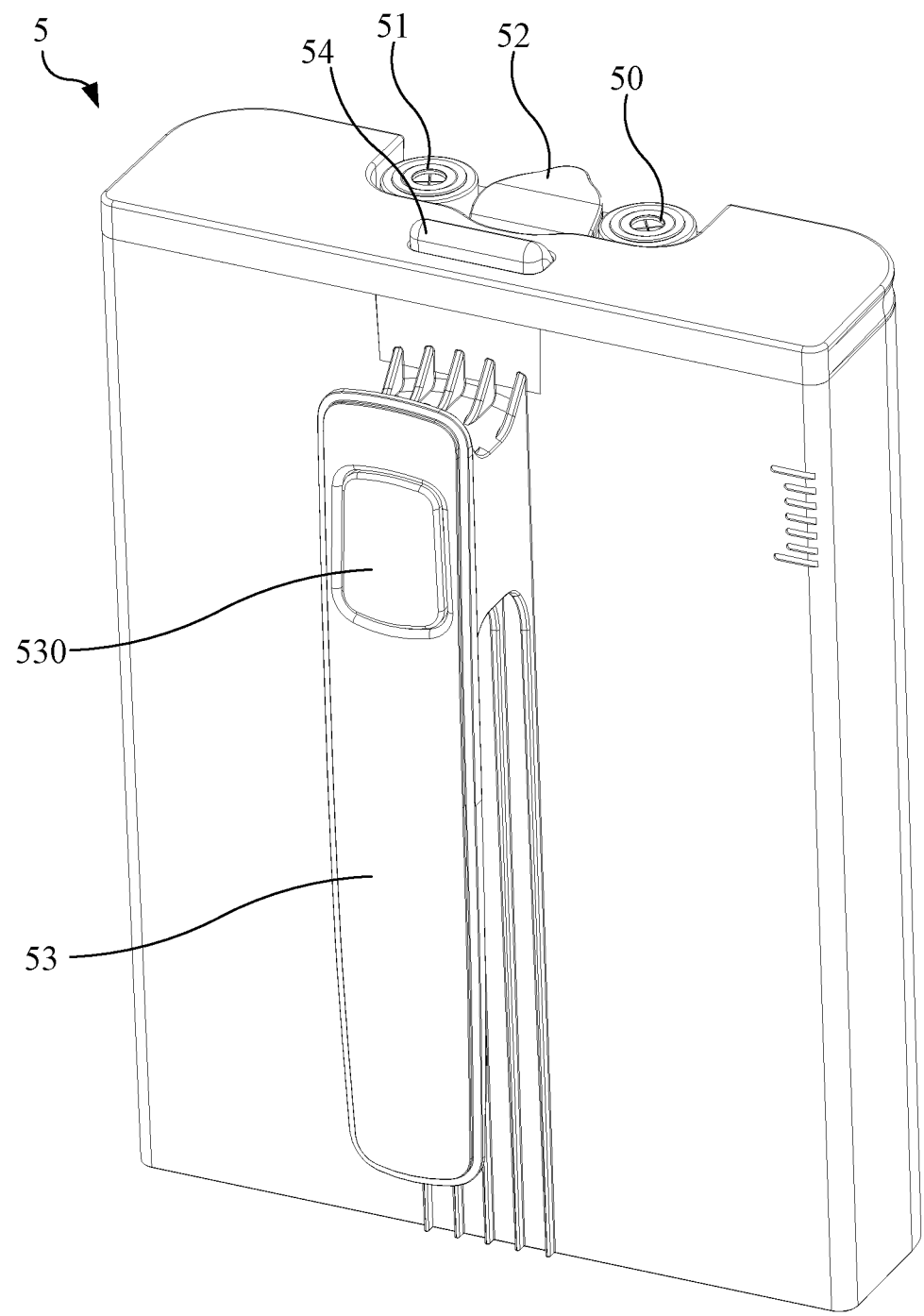
FIG. 17 is an appearance diagram illustrating the water hydrogen module of the integrated hydrogen gas generator according to an embodiment of the present invention.
Figure 18:
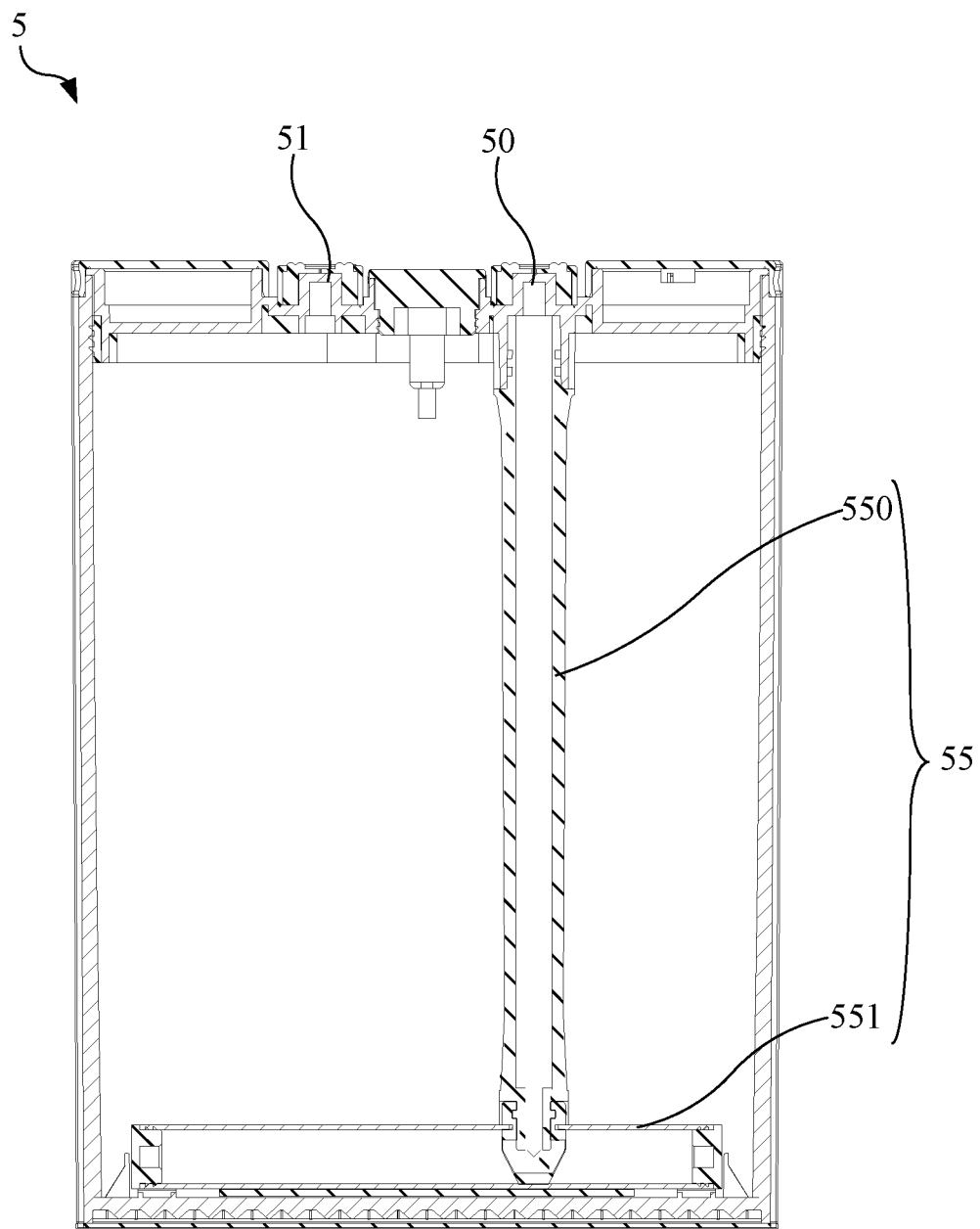
FIG. 18 is a sectional diagram illustrating the hydrogen water module in FIG. 17.

The followings are the detailed descriptions of the hydrogen water module 5. Please refer to FIG. 12, FIG. 13, FIG. 14, FIG. 17 and FIG. 18. FIG. 17 is an appearance diagram illustrating the water hydrogen module 5 of the integrated hydrogen gas generation E according to an embodiment of the present invention. FIG. 18 is a sectional diagram illustrating the water hydrogen module in FIG. 17. As shown in FIG. 17 and FIG. 18, the hydrogen water module 5 further includes a water input/output structure 52, a grip part 53, a telescopic buckle 54 and a gas input rod 55. The water input/output structure 52 is configured to selectively provide a water input/output passage for inputting the water into the hydrogen water module 5 or outputting the hydrogen liquid. The grip part 53 is disposed on one side of the hydrogen water module 5 away from the humidifying module 4, and a linkage button 530 is configured on the grip part 53. The telescopic buckle 54 is linked to the linkage button 530 to selectively couple the hydrogen water module 5 to the integrated passageway device 3.

Furthermore, in practice, the integrated hydrogen gas generator E with the hydrogen water module includes a transfer valve 92 which is disposed between the humidifying passageway 33 and the output passageway 34. When the linkage button 530 drives the telescopic buckle 54, the telescopic buckle 54 blocks the connection of the hydrogen water module 5 with the humidifying passageway 33 and the output passageway 34, and the humidifying passageway 33 is connected to the output passageway 34 by the transfer valve 92. Wherein, the hydrogen water module 5 can be decoupled from the humidifying passageway 33 and the output passageway 34 by the telescopic buckle 54 or by the water input/output structure 52. When the hydrogen water module 5 is coupled to the integrated passageway device 3, the telescopic buckle 54 or the water input/output structure 52 leans against the transfer valve 92, so that the transfer valve 92 will block the path between the humidifying passageway 33 and the output passageway 34. The gas comprising hydrogen in the humidifying passageway 33 must flow into the hydrogen water module 5 through the input structure 55 of the hydrogen water module 5, and then flow into the output passageway 34 from the output structure 51 of the hydrogen water module 5. When the hydrogen water module 5 is taken out, the telescopic buckle 54 and the water input/output structure 52 of the hydrogen water module 5 would not lean against the transfer valve 92, so that the transfer valve 92 directly connect the humidifying passageway 33 and the output passageway 34 without going through the hydrogen water module 5.

The gas input rod 55 includes a hollow column 550 and a porous rod 551. The hollow column 550 is connected to the inputted structure 50 of the hydrogen water module 5. The gas comprising hydrogen is inputted into the gas input rod 55 from the humidifying passageway outlet 331, and then the gas comprising hydrogen flows into the porous rod 551, which is disposed at the bottom of the hydrogen water module 5, through the hollow column 550. The gas comprising hydrogen flows into the hydrogen module 5 from the porous rod 551 to be mixed sufficiently in the liquid in the hydrogen water module 5 to form the hydrogen liquid. Furthermore, the porous rod 551 can have the same structure as the rod 71 of the bubbled stick 7. The remaining gas comprising hydrogen after mixed with the liquid will be outputted to the output passageway 34 from the output structure 51 and the output passageway inlet 340. In another embodiment, the hydrogen water module 5 can accommodate a non-aqueous liquid, resulting in that the gas comprising hydrogen may have a special odor after flowing through the hydrogen water module 5. In order to solve the problem of the special odor, the gas comprising hydrogen outputted from the hydrogen water module 5 can be filtered out the impurities and odors by the filter 6 and then be outputted to the external environment.

Figure 19:
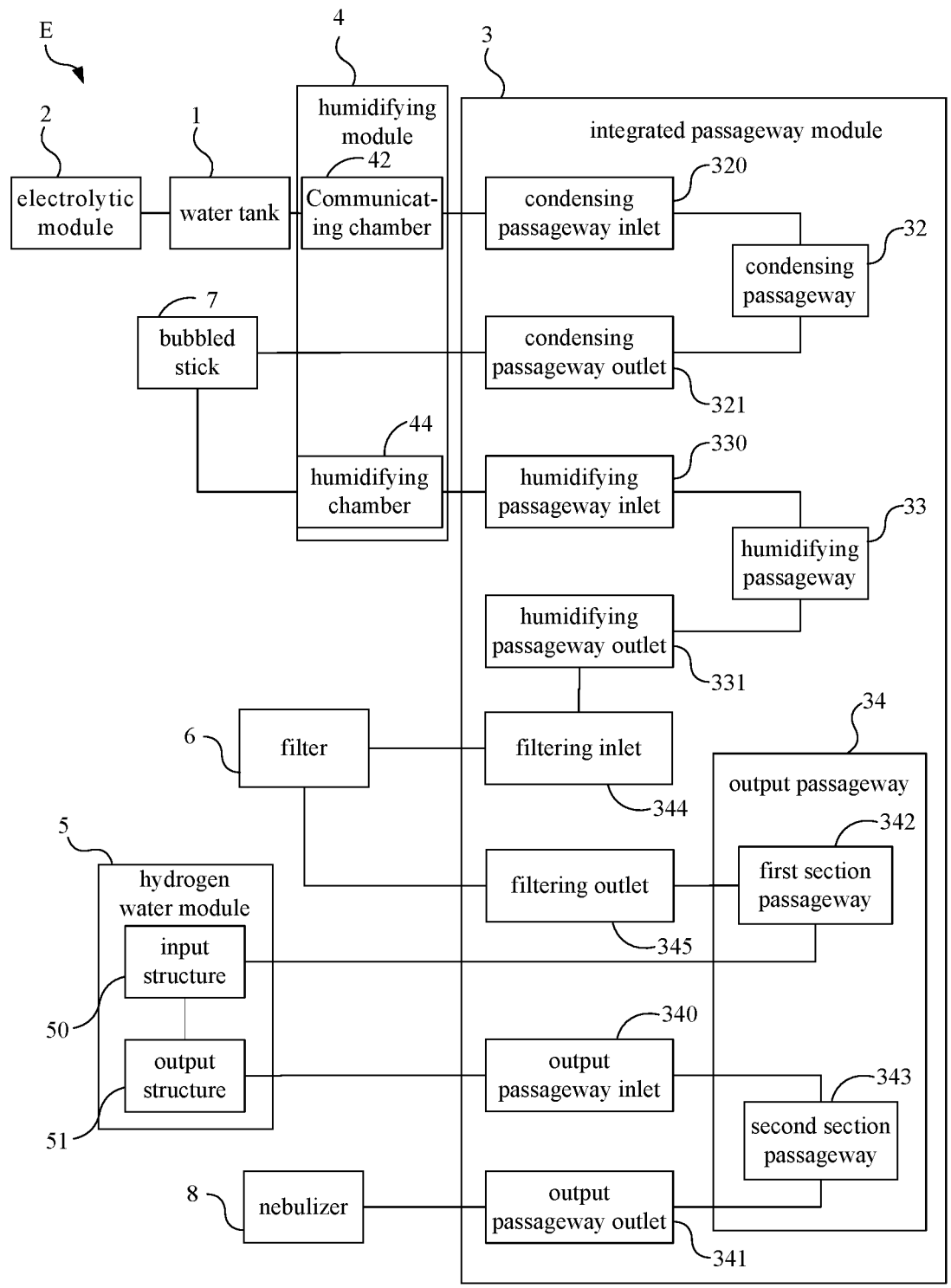
FIG. 19 is function block diagram illustrating the integrated hydrogen gas generator with the hydrogen water module according to another embodiment of the present invention.

The sequence of condensing, humidifying, mixing, filtering, atomizing processes to the gas comprising hydrogen is not limited to the aforementioned embodiments, but can be adjusted without affecting the function of the integrated hydrogen gas generator E with the hydrogen water module. Please refer to FIG. 19. FIG. 19 is functional block diagram illustrating the integrated hydrogen gas generator E with the hydrogen water module according to another embodiment of the present invention. It should be understood that the technical features of the embodiment in FIG. 19 are the same as those described above, except their order. Therefore, the technical features can be deduced by analogy with the aforementioned technical features, and will not be repeated here. As shown in FIG. 19, the humidifying passageway outlet 331 is connected to the filtering inlet 344 to input the humidified gas comprising hydrogen into the filter 6 to be filtered, and then the filtered gas comprising hydrogen flows into the hydrogen water module 5 through the first section passageway 342 of the output passageway 34. In this way, the gas comprising hydrogen flowing into the hydrogen water module 5 would not include impurities, thereby ensuring the hydrogen liquid free from impurities.

Compared to the prior art, the integrated hydrogen gas generator E with the hydrogen water module of the present invention stacks the devices with condensation, humidification, and electrolysis functions in a vertical direction, and uses the integrated formed humidifying module 4 and the integrated formed integrated passageway device 3 to connect the devices. The integrated hydrogen gas generator E of a hydrogen water module of the present invention can operate without additional pipes to connect the devices by the humidifying module 4 engaging with the integrated passageway device 3, thereby avoiding the problems of the cumbersome assembly process of the generator, complicated wiring, large volume of the generator, and dropping, gas leakage, and water leakage problems caused by the pipes.

In addition to the gas comprising hydrogen, the integrated hydrogen gas generator E further has the hydrogen water module 5 to generate the liquid comprising hydrogen, thereby achieving two different functions in one machine. Furthermore, the liquid in the hydrogen water module 5 can be any liquid in addition to water to form the liquid comprising hydrogen, so as to improve the motive for the users to drink the hydrogen liquid.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the meets and bounds of the appended claims.

What is claimed is:

1. An integrated hydrogen gas generator, comprising:
    a water tank configured for containing a water to be electrolyzed;
    an electrolytic module configured for electrolyzing the water and generating a gas comprising hydrogen;
    an integrated passageway module disposed above the water tank, the integrated passageway module comprising an upper cover and a lower cover combined with each other to form a condensing passageway comprising a condensing passageway inlet and a condensing passageway outlet, a humidifying passageway comprising a humidifying passageway inlet and a humidifying passageway outlet, and an output passageway comprising an output passageway inlet and an output passageway outlet;
    a condenser coupled in the condensing passageway of the integrated passageway module for condensing an impurity in the gas comprising hydrogen;
    a humidifying module coupled to the condensing passageway outlet and the humidifying passageway inlet of the integrated passageway module and configured to humidify the gas comprising hydrogen; and
    wherein the gas comprising hydrogen is transmitted among the electrolytic module, the condenser and the humidifying module through the integrated passageway module.

2. The integrated hydrogen gas generator of claim 1, wherein the humidifying module is disposed between the integrated passageway module and the water tank, the humidifying module further has a communicating chamber coupled to the humidifying passageway inlet of the integrated passageway module and the water tank, the electrolytic module is accommodated in the water tank to output the gas comprising hydrogen into the water tank, the gas comprising hydrogen flows to the integrated passageway module through the communicating chamber, and the communicating chamber is decoupled from the humidifying chamber.

3. The integrated hydrogen gas generator of claim 2, further comprising a gas baffle plate assembly disposed in the communicating chamber, the gas baffle plate assembly being configured to reduce or avoid a water vapor and an electrolyte of the gas comprising hydrogen flowing into the condensing passageway of the integrated passageway module.

4. The integrated hydrogen gas generator of claim 1, wherein the upper cover further has a first cap fixed at a position of the upper cover which is above and corresponding to the position of the humidifying passageway outlet, and the first cap movably covers the humidifying passageway outlet to selectively allow the gas comprising hydrogen to flow out of the humidifying passageway outlet or to block water and water vapor from flowing out of the humidifying passageway outlet.

5. The integrated hydrogen gas generator of claim 1, further comprising a filter coupled to the integrated passageway module and configured for filtering the gas comprising hydrogen and a nebulizer coupled to the integrated passageway module and configured to generate an atomized gas to be mixed with the gas comprising hydrogen, wherein the gas comprising hydrogen is transmitted among the electrolytic module, the condenser, the humidifying module, the filter and the nebulizer through the integrated passageway module; wherein the lower cover is an integrally formed structure, and the condenser, the humidifying module, the filter and the nebulizer are directly coupled to the lower cover.

6. The integrated hydrogen gas generator of claim 5, wherein the lower cover further comprises a filtering inlet and a filtering outlet coupled to the filter, the output passageway is divided into a first section passageway and a second section passageway, the first section passageway is coupled to the output passageway inlet and the filtering inlet to input the gas comprising hydrogen to the filter, and the second section passageway is coupled to the filtering outlet and the output passageway outlet to output the filtered gas from the filter; the upper cover further has a second cap fixed at a position of the upper cover which is above and corresponding to the position of the filtering inlet, and the second cap movably covers the filtering inlet to selectively allow the gas comprising hydrogen to flow into the filtering inlet or to block water and water vapor from flowing into the filtering inlet.

7. The integrated hydrogen gas generator of the claim 6, wherein the humidifying module is disposed between the integrated passageway module and the filter, the humidifying module has a input column and a output column, the input column is coupled to the filtering inlet of the lower cover and the filter, and the output column is coupled to the filtering outlet of the lower cover and the filter, the input column and the output column are decoupled from the humidifying chamber; wherein the integrated hydrogen gas generator further comprising a bubbled stick disposed in the humidifying chamber of the humidifying module, the bubbled stick being coupled to the humidifying chamber and the condensing passageway for refining the gas comprising hydrogen from the condensing passageway, so that the gas comprising hydrogen being evenly distributed in the humidifying chamber.

8. The integrated hydrogen gas generator of claim 5, further comprising a hydrogen water module coupled to the integrated passageway module, the hydrogen water module configured for receiving and mixing the gas comprising hydrogen with a liquid accommodated in the hydrogen water module to generate a hydrogen liquid, wherein the gas comprising hydrogen is transmitted among the condenser, the humidifying module, the filter, the hydrogen water module and the nebulizer through the integrated passageway module.

9. The integrated hydrogen gas generator of claim 8, wherein the hydrogen water module further comprises an input structure coupled to the lower cover and coupled to the humidifying passageway outlet to input the gas comprising hydrogen into the liquid to generate the hydrogen liquid, and the hydrogen water module further comprises an output structure coupled to the output passageway inlet for outputting the gas comprising hydrogen, the hydrogen water module further comprises:
 a water input/output structure configured for selectively providing a water input/output channel to allow water to be inputted to the hydrogen water module or to allow the hydrogen liquid to be outputted;
 a grip part disposed on one side of the hydrogen water module away from the humidifying module, the grip part comprising a linkage button being disposed thereon; and
 a telescopic buckle driven by the linkage button, the telescopic buckle being configured to selectively couple the hydrogen water module and the humidifying passageway.

10. The integrated hydrogen gas generator of the claim 9, further comprising a transfer valve disposed between the humidifying passageway and the output passageway, when the linkage button driving the telescopic buckle, the hydrogen water module being decoupled from the humidifying passageway and the output passageway, and the humidifying passageway and the output passageway being coupled to each other through the transfer valve.

11. The integrated hydrogen gas generator of claim 5, wherein the nebulizer has an nebulizer inlet and an nebulizer outlet, the nebulizer inlet being coupled to the output passageway for receiving the gas comprising hydrogen, the nebulizer outlet being couple to external environment, the nebulizer further generating an atomized gas to mix with the gas comprising hydrogen and form a health-care gas, and the health-care gas being outputted to the external environment through the nebulizer outlet.

12. The integrated hydrogen gas generator of claim 11, wherein a surface of the humidifying module is further recessed inward to form a nebulizer accommodating chamber for accommodating the nebulizer.

13. An integrated hydrogen gas generator, comprising:
 a water tank configured for containing a water to be electrolyzed;
 an electrolytic module disposed in the water tank, and being configured for electrolyzing the water to generate a gas comprising hydrogen and outputting into the water tank;
 an integrated passageway module disposed above the water tank, the integrated passageway module comprising an upper cover and a lower cover combined with each other to form a humidifying passageway and an output passageway, and the lower cover being an integrally formed structure;
 a humidifying module disposed above the water tank, the humidifying module coupled to the humidifying passageway of the integrated passageway module and configured to humidify the gas comprising hydrogen; and
 a filter coupled to the integrated passageway module and configured for filtering the gas comprising hydrogen;
 wherein the gas comprising hydrogen is transmitted among the electrolytic module, the humidifying module and the filter through the integrated passageway module.

14. The integrated hydrogen gas generator of the claim 13, further comprising a nebulizer coupled to the integrated passageway module for receiving the gas comprising hydrogen, the nebulizer further generating an atomized gas to mix with the gas comprising hydrogen and form a health-care gas, wherein the gas comprising hydrogen is transmitted among the humidifying module, the filter and the nebulizer through the integrated passageway module.

15. The integrated hydrogen gas generator of the claim 14, wherein the humidifying module, the filter and the nebulizer are directly coupled to the lower cover of the integrated passageway module.

16. The integrated hydrogen gas generator of the claim 13, wherein the integrated passageway module further comprises a condensing space, the condensing space, the humidifying passageway and the output passageway are disposed between the upper cover and the lower cover, the lower cover has a condensing passageway inlet and a condensing passageway outlet coupled by the condensing space, a humidifying passageway inlet and a humidifying passageway outlet coupled by the humidifying passageway, and an output passageway inlet and an output passageway outlet coupled by the output passageway, the condensing passageway inlet is coupled to the water tank for receiving the gas comprising hydrogen, the humidifying module is respectively coupled to the condensing passageway outlet and to the humidifying passageway inlet for humidifying the gas comprising hydrogen and then transporting it to the humidifying passageway.

17. The integrated hydrogen gas generator of the claim 16, further comprising a condensing body which is coupled to the upper cover and is accommodated in the condensing space, the condensing body being combined with the upper cover to form a condenser, which comprises a condensing passageway, and the condensing passageway being coupled to the condensing passageway inlet and to the condensing passageway outlet for condensing the gas comprising hydrogen in the condensing passageway.

18. The integrated hydrogen gas generator of the claim 13, further comprising a hydrogen water module coupled to the integrated passageway module, the hydrogen water module comprising an input structure to input the gas comprising hydrogen to a liquid accommodated by the hydrogen water module, and the hydrogen water module also comprising an output structure for outputting the gas comprising hydrogen, wherein the gas comprising hydrogen is transmitted among the humidifying module, the hydrogen water module and filter through the integrated passageway module.

19. The integrated hydrogen gas generator of the claim 18, wherein the humidifying module, the hydrogen water module and the filter are directly coupled to the lower cover of the integrated passageway module.

\* \* \* \* \*